(12) United States Patent
Niemiec et al.

(10) Patent No.: US 6,419,913 B1
(45) Date of Patent: *Jul. 16, 2002

(54) TOPICAL DELIVERY SYSTEMS FOR ACTIVE AGENTS

(75) Inventors: Susan M. Niemiec, Yardley, PA (US); Jonas C. T. Wang, Robbinsville, NJ (US); Stephen J. Wisniewski, Doylestown, PA (US); Kurt S. Stenn, Princeton; Gwang Wei Lu, Plainsboro, both of NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/916,019

(22) Filed: Jul. 26, 2001

Related U.S. Application Data

(63) Continuation of application No. 09/360,412, filed on Jul. 23, 1999, now Pat. No. 6,284,234.
(60) Provisional application No. 60/095,289, filed on Aug. 4, 1998.

(51) Int. Cl.[7] ................. A61K 31/74; A61K 31/505

(52) U.S. Cl. .................. 424/78.07; 424/78.06; 424/78.03; 424/71; 424/70; 514/275; 514/946; 514/947

(58) Field of Search ................ 514/275, 946, 514/947; 424/71, 70, 78.03, 78.06, 78.07

(56) References Cited

U.S. PATENT DOCUMENTS

| | | | |
|---|---|---|---|
| 4,139,619 A | | 2/1979 | Chidsey, III .................. 424/45 |
| 4,596,812 A | | 6/1986 | Chidsey, III et al. ....... 514/256 |
| 5,629,021 A | * | 5/1997 | Wright ....................... 424/489 |
| 5,837,289 A | * | 11/1998 | Grasela et al. ............... 424/484 |
| 5,945,409 A | * | 8/1999 | Crandall ....................... 514/78 |

FOREIGN PATENT DOCUMENTS

| | | | |
|---|---|---|---|
| DE | 43 30 597 A1 | | 3/1995 |
| EP | 0 431 942 A2 | | 6/1990 |
| JP | 7002677 | | 1/1995 |
| WO | WO 88/01863 | | 3/1988 |
| WO | 92/03123 | * | 3/1992 |
| WO | WO 92/10231 | | 6/1992 |
| WO | WO 94/21262 | | 9/1994 |

OTHER PUBLICATIONS

Niemiec S., Ramachandran C., Weiner N. (1995) Influence of Nonionic Liposomal Composition on Topical Delivery of Peptide Drugs into Pilosebaceous Units: An in Vivo Study Using the Hamster Ear Model. Pharmaceutical Research. 12(8) :1184–1188.

Derwent Publication Ltd., London, GB; An 1997–231136 XP002131769 & JP 09 071513 A (TAISHO PHARM CO LTD), Mar. 18, 1997 abstract.

Roberts J.L. (1987) Androgenetic alopecia: Treatment results with topical minoxidil. Journal of American Academy Dermatology. 16 (3) :705–710.

Gollnick H., Schramm M. (1998) Topical Drug Treatment in Acne. Dermatology:Sebaceous Glands, Acne and Related Disorders. 119–157.

Plewig G., Luderschmidt C. (1977) Hamster Ear Model for Sebaceous Glands. The Journal of Investigative Dermatology. 68:171–176.

Matias J., Orentreich N. (1983) The Hamster Ear Sebaceous Glands. I. Examination of the Regional Variation by Stripped Skin Planimetry. The Journal of Investigative Dermatology. 81:43–46.

Zatz J., (1993) Modification of Skin Permeation by Surface –Active Agents. Skin Permeation Fundamentals and Application: 146–162.

Barry, B.W. (1983) Properties that Influence Percutaneous Absorption. Dermatological Formulations: 127–233.

Schaefer H., Watts F., Brod J., Illel B. (1990) Follicular Penetration. Prediction of Percutaneous Penetration: Methods, Measurements, and Modeling. 163–173.

Roberts J.L. (1997) Androgenetic Alopecia in Men and Women: An Overview of Cause and Treatment. Dermatology Nursing. 9(6) :379–386.

* cited by examiner

Primary Examiner—Theodore J. Criares
Assistant Examiner—Jennifer Kim

(57) ABSTRACT

This invention relates to a method for enhancing the transmembrane penetration of benefit agents using a certain non-ionic lipid/surfactant-containing formulation as an enhancing agent, and the compositions used therein. Various active agents, such as anti-dandruff agents, hair growth agents, hair inhibitor agents, anti-acne agents, anti-aging agents, depilatory agents, and depigmentation agents, may be effectively delivered into the skin, hair follicles and sebaceous glands using the compositions of the present invention.

20 Claims, 9 Drawing Sheets

TOPICAL DELIVERY SYSTEMS FOR ACTIVE AGENTS

CROSS-REFERENCE TO RELATED APPLICATION

This Application is a continuation of U.S. application Ser. No. 09/360,412, filed Jul. 23, 1999 now U.S. Pat. No. 6,284,234, which claims the benefit of U.S. provisional Application No. 60/095,289, filed Aug. 4, 1998, which is incorporated herein in its entirety.

FIELD OF THE INVENTION

This invention relates to a method for the topical delivery of active agents (e.g., drugs), and compositions used therein. More specifically, this invention relates to a method for enhancing the transmembrane penetration of benefit agents using a certain non-ionic lipid/surfactant-containing formulation as an enhancing agent, and the compositions used therein.

BACKGROUND OF THE INVENTION

The topical delivery of an active agent, such as a drug, from a given vehicle is a multistep process which involves; 1) the dissolution, diffusion and/or release of the agent from the vehicle; 2) the transport of the agent to the absorption site; 3) the permeation of the agent through the limiting barrier at the target site; and eventually 4) the elimination of the agent via blood circulation. In order for an active agent to be effectively transported into the epidermal absorption site, the agent must be present at the skin/vehicle interface, be soluble in the available surrounding fluids, and be capable of diffusing down the hair follicle or partitioning into the stratum corneum.

It is well known in the art that the skin presents a formidable barrier to the penetration of active agents due to the presence of the stratum corneum, which is the outermost layer of the skin composed of close packed dead keratinized cells. Thus, the ability of a substance, which is applied to the skin surface, to penetrate through the skin is inversely related to the thickness of the stratum corneum layer.

One known method for enabling the penetration of active agents through the skin is via topical administration. One shortcoming associated with this method is that some active agents, in particular those having a relatively high molecular weight, are not easily absorbed by the skin.

Many methods for enhancing the local penetration of pharmacologically active agents are known in the art. In one approach, surface active agents are included in the pharmacologically active agent-containing formulation. However, this addition of surface active agents results in only a slight to moderate enhancement of permeability at the expense of damaging the barrier skin tissue. See, e.g, Zatz, J. L., Modification of Skin Permeation by Surface-Active Agents in Skin Permeation Fundamentals and Application, 149–162 (1993); and Barry, B. W., *"Properties That Influence Percutaneous Absorption in Dernatological Formulations,"* Percutaneous Absorption, 127–233 (1983). (Addition of "penetration enhancers" increases the permeability of the stratum corneum by disrupting the lipid organization therein.)

Traditionally, the prime pathway for the topical delivery of active agents across the skin was thought to be through intercellular routes and transcellular routes of the stratum corneum. However, alternative means such as via appenageal transport, i.e., follicular transport, is gaining more acceptance in the scientific community. See, e.g., Schaefer, H., et al. Follicular Penetration in Prediction of Percutaneous Penetration: Methods, Measurements, and Modeling, 163–173 (1990)(optimum size for uptake of micro-beads by the skin appendages is between 5–7 $\mu$m). Due to the comparatively lower barrier resistance of the follicles, follicular transport has particular relevance for enabling the delivery of active agents having low diffusion constants, varying solubility characteristics, and/or varying size characteristics.

One of the diseases associated with the hair follicle is androgenetic alopecia ("AGA"), which is the most common cause of hair loss in both men and women and is identifiable by the loss of hair over the vertex of the scalp. Commonly known treatments for AGA include hair follicle transplants, topical therapies, and orally prescribed anti-androgens. See, e.g., J. L. Roberts, *"Androgenetic Alopecia in Men and Women: An Overview of Cause and Treatment,"* 9(6) Dermatology Nursing 379–386 (1997).

Minoxidil is a drug that is often prescribed for the treatment of AGA. Disadvantageously, clinical trials have shown that the topical application of a 2% minoxidil solution to patients experiencing hair loss results stimulated dense hair regrowth in only less than about 5% of the patients and moderate hair regrowth in only about 30% of the patients. See e.g., E. A. Olsen, et al., *"Topical Minoxidil in Early Male Pattem Baldness,"* 13, J. Amer. Acad. Derm. 185–192 (1985); and J. Roberts, *"Androgenetic Alopecia: Treatment With Topical Minoxidil,"* 16(3) J. Amer. Acad. Derm. 705–710 (1987). Moreover, treatments with topical solutions of minoxidil require multiple daily applications, which is not only inconvenient but also expensive.

One known method for the topical administration of minoxidil is via a mousse formulation containing a cellulose derivative film former as disclosed in PCT Patent Application WO 88/01863. Disadvantageously, such cellulose derivatives hinder the diffusion of the minoxidil from the vehicle, which thereby leads to decreased efficacy of the minoxidil.

Various delivery systems are also known in the art for topically delivering anti-acne agents, anti-aging agents, and depigmentation agents to the epidermis and/or dermis. In one method, high levels of alcohol are used to faciliate the delivery of the agent. However, such alcohols disadvantageously tend to extract lipids from the skin surface, which leads to excessively dry skin and irritation. See, e.g. Zatz, J. L. Modification of Skin Permeation by Solvents in Skin Permeation Fundamentals and Application, 146–148 (1993).

It is therefore an object of this invention to provide improved compositions for enabling the topical delivery of pharmacologically active substances without significant adverse side effects on the skin or body membranes. It is also a further object to provide improved compositions for enabling the topical delivery of difficult-to-absorb agents for localized action. It is a further objective to provide an economic, effective topical treatment for hair loss that is convenient to apply. It is yet a further objective to provide improved compositions for enabling the topical delivery of anti-dandruff, depilatory, anti-acne, anti-aging, and depigmentation active agents into the skin.

SUMMARY OF THE INVENTION

In accordance with the present invention, we have found a composition for enhancing the topical delivery of benefit agents comprising, consisting essentially of, or consisting of, based upon the total weight of the composition,:

A. from about 1 percent to about 10 percent of a nonionic lipid selected from
  i. glyceryl monoesters having a fatty acid chain containing from about 3 to about 50 carbon atoms;
  ii. glyceryl diesters having a fatty acid chain containing from about 5 carbon atoms to about 25 carbon atoms;
  iii. alkoxylated alcohols alkoxylated with ethylene oxide or propylene oxide;
  iv. alkoxylated alkyl phenols alkoxylated with ethylene oxide or propylene oxide;
  v. alkoxylated acids alkoxylated with ethylene oxide or propylene oxide;
  vi. alkoxylated amides alkoxyiated with ethylene oxide or propylene oxide;
  vii. alkoxylated sugar derivatives alkoxylated with ethylene oxide or propylene oxide;
  viii. alkoxylated derivatives of natural oils or waxes alkoxylated with ethylene oxide or propylene oxide;
  ix. polyoxyethylene polyoxypropylene block copolymers alkoxylated with ethylene oxide or propylene oxide;
  x. polyoxyethylene fatty ethers having a fatty acid chain containing from about 10 carbon atoms to about 18 carbon atoms;
  xi. steroids;
  xii. fatty acid esters of alcohols where the fatty acid is straight or branched chain having from about 10 carbon atoms to about 20 carbon atoms and the alcohol is straight or branched chain having 1 to 10 carbon atoms; or
  xiii. mixtures thereof;
B. from about 75 percent to about 98 percent of a vehicle solution comprised of:
  1) a first vehicle component comprised of water or a mixture of water and a hydrophilic compound; and
  2) a second vehicle component comprised of an alcohol, a polyol, or mixtures thereof; and
C. an effective amount of the benefit agent(s).

In another embodiment of the present invention, we have found a topical delivery system for active agents comprising, consisting of, or consisting essentially of, based upon the total weight of the delivery system,
A. from about 0.5 percent to about 10 percent, and preferably from about 0.5 percent to about 5 percent, of a nonionic lipid selected from
  i. glyceryl monoesters having a fatty acid chain containing from about 3 to about 50 carbon atoms;
  ii. glyceryl diesters having a fatty acid chain containing from about 5 carbon atoms to about 25 carbon atoms;
  iii. alkoxylated alcohols alkoxylated with ethylene oxide or propylene oxide;
  iv. alkoxylated alkyl phenols alkoxylated with ethylene oxide or propylene oxide;
  v. alkoxylated acids alkoxylated with ethylene oxide or propylene oxide;
  vi. alkoxylated amides alkoxylated with ethylene oxide or propylene oxide;
  vii. alkoxylated sugar derivatives alkoxylated with ethylene oxide or propylene oxide;
  viii. alkoxylated derivatives of natural oils or waxes alkoxylated with ethylene oxide or propylene oxide;
  ix. polyoxyethylene polyoxypropylene block copolymers alkoxylated with ethylene oxide or propylene oxide;
  x. polyoxyethylene fatty ethers having a fatty acid chain containing from about 10 carbon atoms to about 18 carbon atoms;
  xi. steroids;
  xii. fatty acid esters of alcohols where the fatty acid is straight or branched chain having from about 10 carbon atoms to about 20 carbon atoms and the alcohol is straight or branched chain having 1 to 10 carbon atoms; or
  xiii. mixtures thereof; and
B. from about 74 percent to about 99.5 percent of a vehicle solution comprised of:
  1) a first vehicle component comprised of water or a mixture of water and a hydrophilic compound; and
  2) a second vehicle component comprised of an alcohol, a polyol, or mixtures thereof.

In another embodiment of the present invention, we have found a method for enhancing the topical delivery of benefit agents which comprises, consists of, or consists essentially of topically administering to a human or animal the above-described composition. In yet another embodiment of the present invention we have found a method for treating hair loss comprising, consisting of, and/or consisting essentially of topically applying to skin at a desired area for hair induction the above-described composition, wherein the benefit agent is a hair loss treatment agent. In yet another embodiment of the present invention we have found a method for treating the effects of aging comprising, consisting of, and/or consisting essentially of topically applying to skin at a desired area a composition similar to that described with hair growth, but wherein the benefit agent is an anti-aging active agent. In yet another embodiment of the present invention we have found a method for treating acne comprising, consisting of, and/or consisting essentially of topically applying to skin at a desired area for treatment a composition similar to that described with respect to anti-aging, but wherein the benefit agent is an anti-acne active agent. In yet another embodiment of the present invention we have found a method for inducing hair loss comprising, consisting of, and/or consisting essentially of topically applying to skin at a desired area for treatment a composition similar to that described with respect to anti-aging, but wherein the benefit agent is a hair loss inducing active agent. In yet another embodiment of the present invention we have found a method for depigmenting the skin comprising, consisting of, and/or consisting essentially of topically applying to skin at a desired area for treatment a composition similar to that described with respect to anti-aging, but wherein the benefit agent is a depigmentation active agent.

The composition and methods of this invention provide a unique, convenient means for topically delivering benefit agents with minimal skin irritation, and when the active substance is minoxidil or mixtures thereof, the composition and methods of this invention provide an effective, economical method for treating hair loss resulting from alopecia. In addition, when the composition contains an effective amount of anti-acne agent, the composition and methods of this invention provide an effective, economic means for treating acne. Similarly, when the composition contains an effective amount of an anti-dandruff agent, a depilatory agent, an anti-aging agent or a depigmentation agent, the composition and methods of this invention provide an effective, economic means for treating the symptoms of dandruff, removing hair, preventing the signs of aging and depigmenting the skin, respectively.

Other features and advantages of the present invention will be apparent from the detailed description of the invention and from the claims.

BRIEF DESCRIPTION OF THE DRAWINGS

The invention will be more fully understood and further advantages will become apparent when reference is made to the following detailed description of the invention and the accompanying drawings in which.

DETAILED DESCRIPTION OF THE INVENTION

Figure 1A:
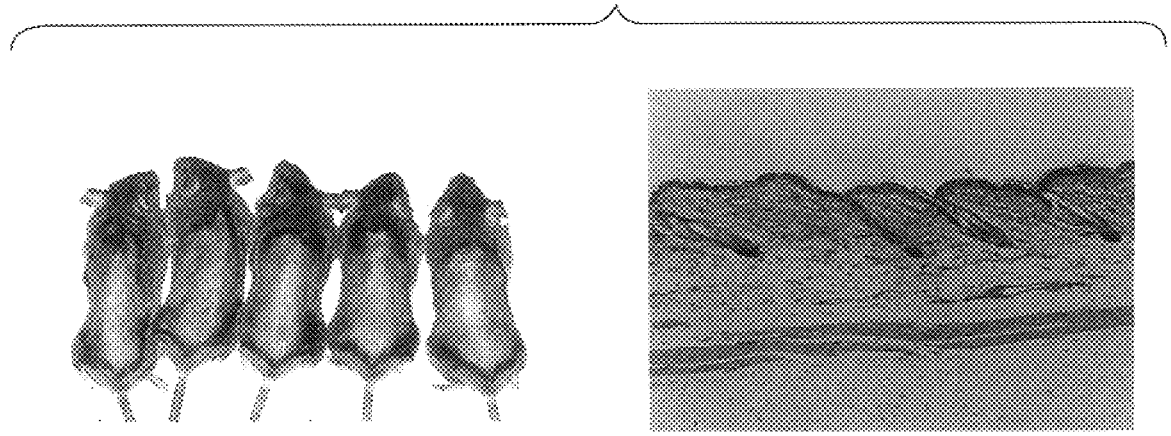
FIG. 1(A) is a representation of the dorsal view of the skin of C3H mice taken 19 days after topical application of a formulation comprised of the 2% minoxidil-containing solution of Example 1 thereto, and the corresponding histological view associated therewith.

It is believed that one skilled in the art can, based upon the description herein, utilize the present invention to its fullest extent. The following specific embodiments are to be construed as merely illustrative, and not limitive of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The first compound of the composition of the present invention is a non-ionic lipid such as glyceryl monoesters having a fatty acid chain containing from about 3 to about 50 carbon atoms, and preferably from about 10 to about 18 carbon atoms; glyceryl diesters having a fatty acid chain containing from about 5 carbon atoms to about 25 carbon atoms, and preferably from about 10 carbon atoms to about 18 carbon atoms; alkoxylated alcohols; alkoxylated alkyl phenols; alkoxylated acids; alkoxylated amides; alkoxylated sugar derivatives; alkoxylated derivatives of natural oils or waxes; polyoxyethylene polyoxypropylene block copolymers; polyoxyethylene ether fatty acids having a fatty acid chain containing from about 10 carbon atoms to about 18 carbon atoms; steroids; fatty acid esters of alcohols where the fatty acid is straight or branched chain having from about 10 carbon atoms to about 20 carbon atoms and the alcohol is straight or branched chain having 1 to 10 carbon atoms; and mixtures thereof, wherein the alkoxylated lipids are alkoxylated with ethylene oxide or propylene oxide, with ethylene oxide being preferred.

Examples of suitable glyceryl monoesters include, but are not limited to, glyceryl caprate, glyceryl caprylate, glyceryl cocate, glyceryl erucate, glyceryl hydroxysterate, glyceryl isostearate, glyceryl lanolate, glyceryl laurate, glyceryl linolate, glyceryl myristate, glyceryl oleate, glyceryl PABA, glyceryl palmitate, glyceryl ricinoleate, glyceryl stearate, glyceryl thiglycolate, and mixtures thereof, with glyceryl laurate and glyceryl myristate being preferred.

Examples of suitable glyceryl diesters include, but are not limited to, glyceryl dilaurate, glyceryl dioleate, glyceryl dimyristate, glyceryl disterate, glyceryl sesuioleate, glyceryl stearate lactate, and mixtures thereof, with glyceryl dilaurate and glyceryl dimyristate being preferred.

Examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. Preferred polyoxyethylene fatty ethers include polyoxyethylene stearyl ether, polyoxyethylene myristyl ether, and polyoxyethylene lauryl ether having from about 3 to about 10 oxyethylene units.

Examples of suitable steroids include, but are not limited to, cholesterol, betasitosterol, bisabolol, and mixtures thereof.

Examples of suitable fatty acid esters of alcohols include isopropyl myristate, aliphati-isopropyl n-butyrate, isopropyl n-hexanoate, isopropyl n-decanoate, isoproppyl palmitate, octyidodecyl myristate.

Exemplary alkoxylated alcohols useful as the nonionic lipid in the compositions of the invention have the structure shown in formula I below:

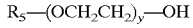  Formula I wherein $R_5$ is a branched or unbranched alkyl group having from about 6 to about 22 carbon atoms and y is between about 4 and about 100, and preferably, between about 10 and about 100. A preferred alkoxylated alcohol is the species wherein $R_5$ is a lauryl group and y has an average value of 23, which is known by the CTFA name "laureth 23" and is available from ICI Americas, Inc. of Wilmington, Del. under the tradename, "BRIJ 35."

Another exemplary alkoxylated alcohol is an ethoxylated derivative of lanolin alcohol. Lanolin alcohol is a mixture of organic alcohols obtained from the hydrolysis of lanolin. An example of an ethoxylated derivative of lanolin alcohol is laneth-10, which is the polyethylene glycol ether of lanolin alcohol with an average ethoxylation value of 10.

Another exemplary alkoxylated alcohol is polyoxypropylene polyoxyethylene alkyl ether, the structure of which is shown schematically in formula II below:

Formula II wherein x:q is about 2:2 to about 38:37. An exemplary member of this class of materials is the material known by the CTFA name "PPG-12-Buteth-16," which conforms to structure II above wherein R is a butyl group, x has an average value of 12 and y has an average value of 16. This material is available from Amerchol Corp. of Edison, N.J. under the tradename, "UCON Fluid 50-HB-660."

Another type of non-ionic lipids include alkoxylated alkyl phenols, which generally conform to the structure:

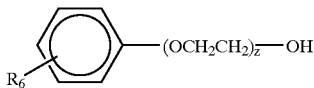

Formula III wherein $R_6$ is a branched or unbranched alkyl group having about 6 to about 22 carbon atoms and z is between about 7 and 120, and preferably, between about 10 and about 120. An especially preferred member of this class of materials is the species wherein $R_6$ is a nonyl group and z has an average value of about 14. This material is known by the CTFA name "nonoxynol-14" and is available under the tradename, "MAKON 14" from the Stepan Company of Northfield, Ill.

Another type of non-ionic lipids include alkoxylated acids, which are esters of an acid, most usually a fatty acid, with a polyalkylene glycol. An exemplary material of this class has the CTFA name "PEG-8 laurate," and the following structure shown in formula IV.:

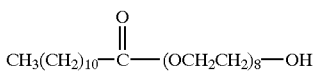

Formula IV

Another type of non-ionic lipids includes the alkoxylated amides that may conform to one or both of structures V or VI shown below:

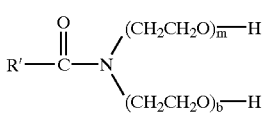

Formula V

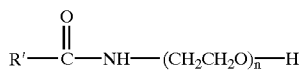

Formula VI wherein n is from about 8 to about 100 and the sum of m plus b is from about 8 to about 100. An exemplary member of this class is known by the CTFA name "PEG-6 Cocoamide," which conforms generally to structure V wherein R'CO represents the fatty acids derived from coconut oil and n has an average value of about 6.

Another type of non-ionic lipids includes the alkoxylated sugar derivatives. An exemplary member of this class, which is known by the CTFA name "Polysorbate 20," is a mixture of laurate esters of sorbitol and sorbitol anhydrides, consisting predominately of the monoester, condensed with about 20 moles of ethylene oxide. This material is available under the tradename "TWEEN 20" from ICI Americas of Wilmington, Del.

Another example of an alkoxylated sugar derivative useful in the compositions of the invention is PEG-20 methyl-glucose sesquistearate, which is the polyethyleneglycol ether of the sesquiester of methyl glucose and stearic acid, contains an average of 20 moles of ethylene oxide, and is available under the tradename, "Glucamate SSE-20" from the Amerchol Corp. of Edison, N.J.

Another type of non-ionic lipids includes the alkoxylated derivatives of natural oils and waxes. Examples of this class of material include PEG40 lanolin, PEG-40 castor oil and PEG-40 hydrogenated castor oil.

Another type of non-ionic lipids includes polyoxyethylene polyoxypropylene block copolymers. These materials are generally known by the CTFA name, "Poloxamer" and conform to the structure VII.:

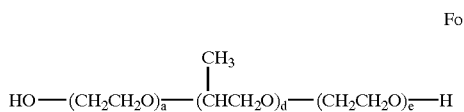

Formula VII wherein a:d:e is from about 2:16:2 to about 98:67:98. Exemplary members of this class of materials useful in the compositions of the invention are "Poloxamer 101" and "Poloxamer 182," in which a, d, and e have average values of 2, 16 and 2 and 8, 30 and 8, respectively.

Preferred nonionic lipids include polyoxyethylene fatty ethers, glyceryl diesters, and mixtures thereof. More preferred nonionic lipids include polyoxyethylene stearyl ether, polyoxyethylene myristyl ether, and polyoxyethylene lauryl ether, glyceryl dilaurate, glyceryl dimystate, glyceryl distearate, and mixtures thereof, whereby each ether has from about 5 to about 10 oxyethylene units.

In an embodiment wherein the reduction of skin irritation is a concern, it is preferable to use a nonionic lipid having a greater amount of carbon atoms on the hydrophilic head group moiety, or in the alternative, a nonionic lipid having a greater amount of carbon atoms on the hydrophobic fatty acid chain moiety. The former can be achieved by increasing the amount of carbon atoms on the head group of, for example, a polyoxyethylene-10-stearyl ether from about 10 carbon atoms to from about 15 to 20 carbon atoms. The latter can be achieved by increasing the amount of carbon atoms on the 12 carbon fatty acid tail of, for example, glyceryl diesters to from about 14 carbons to about 16 carbons.

The composition of the present invention includes, based upon the total weight of the composition, from about 1 percent to about 10 percent, and preferably from about 3 percent to about 7 percent of the nonionic lipid.

The second compound in the composition is a vehicle solution comprised of a first vehicle component and a second vehicle component. The first vehicle component may be comprised of water, or a mixture of water and a hydrophilic compound such as soymilk. The second vehicle component may be comprised of an alkanol, a polyol, or mixtures thereof. Mixtures of water and both an alkanol and a polyol are preferred, with mixtures of water, alkanols having from about 2 to about 4 carbon atoms, and polyols having from about 2 to about 10 carbon atoms being more preferred. Mixtures of water, ethanol, and propylene glycol are most preferred. For anti-aging applications it is preferable to use a mixture of water along with the alkanol and/or polyol.

The vehicle solution is present in an amount, based upon the total weight of the composition, from about 74 percent to about 98 percent, preferably from about 80 percent to about 95 percent, and more preferably from about 86 percent to about 92 percent.

Suitable alkanols are those having from about 2 carbon atoms to about 12 carbon atoms, and preferably from about 2 carbon atoms to about 4 carbon atoms, with ethanol being the most preferred.

Suitable polyols are those having from about 2 carbon atoms to about 15 carbon atoms, and preferably from about 2 carbon atoms to about 10 carbon atoms and may include, but not be limited to propylene glycol, polyethylene glycol, diethylene glycol, triethylene glycol, glycerol, hexanetriol and copolymers or mixtures thereof. A preferred polyol is propylene glycol.

The alkanols, polyols, or mixtures thereof may be present in the vehicle solution in an amount, based upon the total weight of the vehicle solution, of from about 35 percent to about 90 percent, and preferably from about 70 percent to about 90 percent.

Water is present in the vehicle solution in an amount, based upon the total weight of the vehicle solution, of from about 5 percent to about 50 percent, and preferably from about 10 percent to about 30 percent. In a preferred embodiment wherein minoxidil is the active substance, water is present in an amount, based upon the total weight of the vehicle solution, of from about 20% to about 50%, and preferably from about 20% to about 40%.

In a preferred embodiment, the vehicle solution contains, based upon the total weight of the vehicle solution, water, alcohol, and a polyol in a ratio of about 1 to about 10 (water); about 3 to about 10 (alcohol); about 1 to about 10 (polyol), respectively. More preferably, the vehicle solution contains, based upon the total weight of the vehicle solution, water, ethanol, and polyethylene glycol in a ratio of about 1 to about 4 (water); about 2 to about 3 (ethanol) and about 1 to about 4 (polyethylene glycol), respectively.

In one embodiment, the non-ionic lipid and vehicle solution may be combined by initially heating the non-ionic lipid at ambient pressure to a temperature above its melting point for a period of time until the lipid is substantially melted. Typically this temperature may be from about 30° C. to about 80° C., and the period of time may be from about 1 minute to about 5 minutes. After the lipid is melted, the second vehicle component is added thereto at the elevated temperature, then the resulting mixture is cooled to 25° C. The first vehicle component is then added to the resulting mixture at ambient temperature and pressure.

In a preferred embodiment using a second vehicle component comprised of an alcohol and a polyol, only the alcohol is added to the melted lipid at the elevated temperature in order to enhance the solubility of the lipid. Then, the polyol and water are added thereto at ambient temperature and pressure conditions.

The non-ionic lipid and the vehicle solution of the present invention are preferably combined with a benefit agent. By "benefit agent," it is mean any active ingredient that is to be delivered into and/or onto the skin at a desired location, such as a cosmetic agent or a pharmaceutical agent. By "cosmetic agent," it is meant any ingredient that is appropriate for cosmetically treating, providing nutrients to, and/or conditioning the hair and/or skin via topical application. By "pharmaceutical agent," it is mean any drug that is either hydrophobic or hydrophilic in nature and appropriate for topical use. As used herein "medicament agents" include those agents capable of promoting recovery from injury and illness.

Examples of suitable benefit agents include, but are not limited to, depigmentation agents; reflectants; humectants; antimicrobial (e.g., antibacterial) agents; allergy inhibitors; anti-acne agents; anti-aging agents; anti-wrinkling agents, antiseptics; analgesics; antitussives; antipruritics; local anesthetics; anti-hair loss agents; hair growth promoting agents; hair growth inhibitor agents, antihistamines; antiinfectives; inflammation inhibitors; anti-emetics; anticholinergics; vasoconstrictors; vasodilators; wound healing promoters; peptides, polypeptides and proteins; deodorants and antiperspirants; skin emollients and skin moisturizers; hair conditioners; hair softeners; hair moisturizers; tanning agents; skin lightening agents; antifungals such as antifungals for foot preparations; depilating agents; external analgesics; counterirritants; hemorrhoidals; insecticides; poison ivy products; poison oak products; burn products; anti-diaper rash agents; prickly heat agents; make-up preparations; vitamins amino acids and their derivatives; herbal extracts; retinoids; flavoids; sensates; anti-oxidants; skin conditioners; hair lighteners; chelating agents; cell turnover enhancers; coloring agents; sunscreens and the like, and mixtures thereof. The amount of certain cleansing composition/delivery system compounds for the benefit agent purposes set forth below is in addition to the amount of the same compound that may be desired for use in the cleansing composition/delivery system therefor.

Examples of suitable reflectants nonexclusively include mica, alumina, calcium silicate, glycol dioleate, glycol distearate, silica, sodium magnesium fluorosilicate, and mixtures thereof.

Examples of suitable UV absorbers include benzophenone, bomelone, butyl paba, cinnamidopropyl trimethyl ammonium chloride, disodium distyrylbiphenyl disulfonate, paba, potassium methoxycinnamate, and mixtures thereof.

Commercially available humectants which are capable of providing moisturization and conditioning properties to the cleansing composition are suitable for use in the present invention. The humectant is preferably present in an amount of from about 0 percent to about percent, more preferably from about 0.5 percent to about 5 percent, and most preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, pentylene glycol, dipropylene glycol, and mixtures thereof; 2) polyalkylene glycol of the formula VIII:

$$HO\text{-}(R''O)_r\text{-}H \qquad \text{Formula VIII}$$

wherein R" is an alkylene group having from about 2 to about 4 carbon atoms and r is an integer of from about 1 to about 10, such as PEG 4; 3) polyethylene glycol ether of methyl glucose of formula IX:

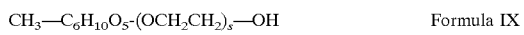
$$CH_3-C_6H_{10}O_5-(OCH_2CH_2)_s-OH \qquad \text{Formula IX}$$

wherein s is an integer from about 5 to about 25; 4) urea; 5) fructose; 6) glucose; 7) honey; 8) lactic acid; 9) maltose; 10) sodium glucuronate; and 11) mixtures thereof, with glycerine being the preferred humectant.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, caprylol collagen amino acids; capryloyl kertain amino acids; capryloyl pea amino acids; cocodimonium hydroxypropyl silk amino acids; corn gluten amino acids; cysteine; glutamic acid; glycine; hair keratin amino acids; hair amino acids such as aspartic acid, threonine, serine, glutamic acid, proline, glycine, alanine, half-cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof Suitable peptides, polypeptides, and proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; keratin; milk protein; protease; serum protein; silk; sweet almond protein; wheat germ protein; wheat protein; wheat protein, alpha and beta helix of keratin proteins; hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Examples of suitable vitamins nonexclusively include vitamin B complex; including thiamine, nicotinic acid, biotin, pantothenic acid, choline, riboflavin, vitamin B6, vitamin B12, pyridoxine, inositol, camitine; vitamins A,C, D,E,K and their derivatives such as vitamin A palmitate and pro-vitamins, e.g. (i.e. panthenol (pro vitamin B5) and panthenol triacetate) and mixtures thereof.

Examples of suitable antibacterial agents nonexclusively include bacitracin, erythromycin, neomycin, tetracycline, chlortetracycline, benzethonium chloride, phenol, and mixtures thereof.

Examples of suitable skin emollients and skin moisturizers nonexclusively include mineral oil, lanolin, vegetable oils, isostearyl isostearate, glyceryl laurate, methyl gluceth 10, methyl gluceth 20 chitosan, and mixtures thereof.

Examples of suitable hair conditioners nonexclusively include quatemized compounds such as behenamidopropyl PG-dimonium chloride, tricetylammonium chloride, dihydrogenated tallowamidoethyl hydroxyethylmonium methosulfate, and mixtures thereof as well as lipophilic compounds like cetyl alcohol, stearyl alcohol, hydrogenated polydecene, and mixtures thereof.

An example of a suitable hair softener nonexclusively includes silicone compounds, such as those that are either non-volatile or volatile and those that are water soluble or water insoluble. Examples of suitable silicones include organo-substituted polysiloxanes, which are either linear or cyclic polymers of monomeric silicone/oxygen monomers and which nonexclusively include cetyl dimethicone; cetyl triethylammonium dimethicone copolyol phthalate; cyclomethicone; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone; and mixtures thereof.

Examples of suitable hair moisturizers nonexclusively include panthenyl ethyl ether, phytantriol, and mixtures thereof.

Examples of sunscreen agents nonexclusively include butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl. anthranilate, aminobenzoic acid, cinoxate, diethanolamine methoxycinnamate, glyceryl aminobenzoate, titanium dioxide, zinc oxide, oxybenzone, padimate o, red petrolatum, and mixtures thereof.

An example of a suitable tanning agent nonexclusively includes dihydroxyacetone.

Examples of skin lightening agents nonexclusively include hydroquinone, catechol and its derivatives, ascorbic acid and its derivatives, and mixtures thereof.

Examples of suitable insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET; compounds of the formula X:

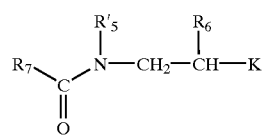

Formula X wherein $R'_5$ is a branched or unbranched alkyl group having about 1 to about 6 carbon atoms, $R_6$ is H, methyl or ethyl, $R_7$ is a branched or unbranched alkyl or alkoxy group having from about 1 to about 8 carbon atoms, and K is a —CN or a —COOR$_6$ group, wherein $R_6$ is a branched or unbranched alkyl group having from about 1 to about 6 carbon atoms; natural or synthetic pyrethroids, whereby the natural pyrethroids are contained in pyrethrum, the extract of the ground flowers of *Chrysanthemum cinerariaefolium* or *C coccineum*; and mixtures thereof. Within the structure of Formula XI. are ethyl 3-(N-butylacetamido)propionate, wherein $R_7$ is a CH$_3$ group, $R'_5$ is an n-butyl group, $R_6$ is H, K is COOR$_8$ and $R_8$ is ethyl, which is available commercially from Merck KGaA of Darmstadt, Germany under the name, "Insect Repellent 3535."

An example of an anti fungal for foot preparations nonexclusively includes tolnaftate.

Examples of suitable depilating agents nonexclusively include calcium thioglycolate, magnesium thioglycolate, potassium thioglycolate, strontium thioglycolate, and mixtures thereof.

Examples of suitable external analgesics and local anesthetics nonexclusively include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone.

Examples of suitable hemorrhoidal products nonexclusively include the anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

Examples of suitable make-up preparations nonexclusively include components for lipstick, rouge, blush, eye liner, eyeshadow powder, mascara, face powder, and mixtures thereof.

One preferred type of benefit agent includes those therapeutic components that are effective in the treatment of dandruff, seborrheic dermatitis, and psoriasis as well as the symptoms associated therewith. Examples of such suitable benefits agents nonexclusively include zinc pyrithione, shale oil and derivatives thereof such as sulfonated shale oil, selenium sulfide, sulfur; salicylic acid; coal tar; povidone-iodine, imidazoles such as ketoconazole, dichlorophenyl imidazolodioxalan, which is commercially available from Janssen Pharmaceutica, N.V., under the tradename, "Elubiol", clotrimazole, itraconazole, miconazole, climbazole, tioconazole, sulconazole, butoconazole, fluconazole, miconazolenitrite and any possible stereo isomers and derivatives thereof such as anthralin; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

The amount of benefit agent to be combined with the composition of the present invention may vary depending upon, for example, the benefit agent being used, the resulting benefit desired and the sensitivity of the user to the benefit agent. Unless otherwise expressed herein, preferably the benefit agent is present in the cleansing composition or delivery system in an amount, based upon the total weight of the composition, from about 0.001 percent to about 20 percent, and preferably from about 0.001 percent to about 10 percent, and more preferably from about 0.001 percent to about 5 percent.

As stated above, pharmaceutical agents include a broad class of chemical and therapeutic agents which are sufficiently potent such that they can be delivered into the skin or mucous membranes in sufficient quantities to produce the desired therapeutic effect. In general, this includes therapeutic agents in all of the major therapeutic areas including, but not limited to, anti-infectives, such as antibiotics and antiviral agents, analgesics and analgesic combinations, antiarthritics, antidepressants, antidiabetic agents, antihistamines, anti-inflammatory agents, antimigraine preparations, antinauseants, antineoplastics, antipruritics, antipsychotics, xanthine derivatives, cardiovascular preparations including calcium channel blockers, beta-blockers, antiarrhythmics, antihypertensives, diuretics, vasodilators including general, coronary, peripheral and cerebral; hormones, immunosuppressives, and muscle relaxants.

In particular, the pharmaceutical agent is present in sufficient amounts to enable its delivery into the skin and/or philosebaceous units, i.e. hair follicles having sebaceous glands, to produce the desired therapeutic effect. Typically, that amount may range, based upon the total weight of the composition, from about 0.01 percent to about 20 percent, and preferably from about 2 percent to about 5 percent.

Many of the benefit agents of the present invention may be classified as one or more of the following: anti-acne agents, anti-aging agents, depigmentation agents, hair growth inducing agents, hair loss inhibiting agents, and hair growth prohibiting agents.

Preferred benefit agents include 6-(1-piperidinyl)-2,4-pyrimidinediamine-3-oxide, which is also known as minoxidil and is described in U.S. Pat. Nos. 4,139,619 and 4,596,812, the disclosures of which are incorporated by reference herein in their entireties; retinoids (e.g., retinol) and derivatives thereof; imidazoles such as ketoconazole, elubiol, econazole, itraconazole, miconazole; other anti-fungals include clortrimazole, terconazole, tioconazole, fluconazole, butoconazole, oxiconazole, and sulconazole; 5 alpha-reductase inhibitors such as finasteride; or mixtures thereof.

Most preferred benefit agents nonexclusively include sulfonated shale oil, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylammonium chloride, polyquatemium 10, panthenol, panthenol triacetate, vitamin A and derivatives thereof (e.g., tretinoin), vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, erthromycin, and mixtures thereof.

A preferred embodiment includes the following benefit agents: 1) a mixture of ketoconazole and minoxidil at a weight ratio of about 0.1 part to about 10 parts, and preferably from about 0.5 parts to about 5 parts ketoconazole: about 1 part to about 5 parts minoxidil; and 2) a mixture of finasteride and minoxidil at a weight ratio of about 1 part to about 10 parts, and preferably from about 0.5 parts to about 5 parts finasteride: about 1 part to about 5 parts minoxidil.

In one embodiment directed towards the treatment of hair loss, one preferred active substance includes minoxidil in combination with an alpha hydroxy acid, such as, for example lactic acid and/or glycolic acid, andlor a sulfonated molecule such as, for example sodium sulfate,at a minoxidil:alpha hydroxy acid:sulfonated molecule weight ratio of about 1:1:0 to about 1:10:10 or about 1:0:1 to about 1:10:10.

In a preferred embodiment in which the active component is minoxidil, a suitable amount of minoxidil is, based upon the total weight of composition, from greater than about 0 percent to about 20 percent, and preferably from about 1 percent to about 5 percent.

The vehicle solution and non-ionic lipid, when combined with the benefit agent, are present in an amount effective to enable a sufficient amount of the benefit agent into the skin. While the amount of vehicle solution and non-ionic lipid used will vary with the type and amount of benefit agent available, the intended usage of the final composition, i.e. therapeutic versus maintenance regimen, and sensitivity of the individual user to the composition, typically the weight ratio of non-ionic lipid: benefit agent may vary from about 1 to about 20 parts non-ionic lipid: to about 0.1 to about 20 parts benefit agent, and preferably from about 1 to about 5 parts non-ionic lipid: to about 0.1 to about 10 parts benefit agent. The weight ratio of vehicle solution: benefit agent may vary from about 1 to about 95 parts vehicle solution: to about 0.1 to about 20 parts benefit agent, and preferably from about 50 to about 95 parts vehicle solution: to about 0.1 to about 5 parts benefit agent The non-ionic lipid, the vehicle solution, and the benefit agent may be combined under ambient conditions via any conventional mixing apparatus known in the art, although it is preferable to produce a lipid-second vehide component premixture as aforementioned. The resulting combination possesses particle sizes in the range of about 1 nm to about 500 nm, and preferably from about 1 nm to about 20 nm. In one preferred embodiment wherein the composition contains both a polyol and an alcohol at a cumulative concentration that is less than or about equal to that of the hydrophilic component, the resulting composition is micellar in nature.

The composition of this invention can be formulated in a variety of dosage forms for topical application that include, but are not limited to, for example, lotions, creams, ointments, sprays, aerosols, skin patches, soap, mousses, tonics, gels or the like which is designed to be left on the skin and not washed shortly after application. Altemafively, the composition may be applied to the desired area in the form of, for example, a lotion, cream, gel, soap, shampoo or the like which is designed to be rinsed off within a given amount of time after application.

Another embodiment of the present invention is directed to a method for enhancing the topical application of benefit agents which comprises topically administering to a human or animal a composition as described above.

While the amount of the vehicle solution and non-ionic lipid to be applied will depend upon, for example, the type and amount of benefit agent available, the intended usage of the final composition, i.e. therapeutic versus maintenance regimen, and sensitivity of the individual user to the composition, typically the composition of the present invention should be topically applied to affected body parts at regular intervals, and preferably from about 5 to about 7 times per week. More preferably, the composition is applied more frequently during the initial stages of treatment, e.g. from about 5 to about 7 times per week until the desired effect is achieved, then less frequently when maintenance is desired, e.g. from about 3 to about 5 times per week.

In a preferred embodiment wherein the composition is incorporated into a shampoo, the shampoo is applied to wet hair, and the hair is washed in accordance with known practices. More preferably, the composition remains on the hair for greater than about 0 to about 10 minutes, and preferably from about 4 to about 7 minutes before rinsing.

An alternative preferred embodiment of the present invention is directed to a method for treating hair loss, such as hair loss resulting from alopecia, comprising topically applying to skin at a desired area for hair regrowth the above-described composition wherein the active substance is comprised of an effective amount of a hair loss treatment agent such as minoxidil or mixture thereof. As used herein, "hair loss treatment agents" shall include agents capable of growing hair and/or agents capable of preventing the loss of hair. In a preferred embodiment, the composition contains, based upon the total weight of the composition, from about 0.1 percent to about 20 percent, and preferably from about 1 percent to about 5 percent hair loss treatment agent.

Examples of benefit agents suitable for treating hair loss include, but are not limited to potassium channel openers or peripheral vasodilators, such as minoxidil, diazoxide, and compounds such as N"-cyano-N-(tert-pentyl)-N'-3-pyridinyl-guanidine ("P-1075") as disclosed in U.S. Pat. No. : 5,244,664, which is incorporated herein by reference; vitamins, such as vitamin E and vitamin C, and derivatives thereof such as vitamin E acetate and vitamin C palmitate; hormones, such as erythropoietin, prostaglandins, such as protaglandin E1 and protaglandin F2-alpha; fatty acids, such as oleic acid; diluretics such as spironolactone; heat shock proteins ("HSP"), such as HSP 27 and HSP 72; calcium channel blockers, such as verapamil HCL, nifedipine, and diltiazemamiloride; immunosuppresent drugs, such as cyclosporin and Fk-506; 5 alpha-reductase inhibitors such as finasteride; growth factors such as, EGF, IGFand FGF; transforming growth factor beta; tumor necrosis factor; non-steroidal anti-inflammatory agents such as benoxaprofen; retinoids such as tretinoin: cytokines, such as IL-6, IL-1alpha, and IL-1beta; cell adhesion molecules such as ICAM; glucorcorticoids such as betametasone; botanical extracts such as aloe, clove, ginseng, rehmannia, swertia, sweet orange, zanthoxylum, Serenoa repens (saw palmetto), Hypoxis rooperi, stinging nettle, pumpkin seeds, and rye pollen; other botanical extracts including sandlewood, red beet root, chrysanthemum, rosemary, burdock root and other hair growth promoter activators which are disclosed in DE 4330597 which is incorporated by reference in its entirety herein; homeopathic agents such as Kalium Phosphoricum D2, Azadirachta indica D2, and Joborandi D1; genes for cytokines, growth factors, and male-pattern baldness; antifungals such as ketoconazole, and elubiol; antibiotics such as streptomycin; proteins inhibitors such as cycloheximide; acetazolamide; benoxaprofen; cortsone; diltiazem; hexachlorobenzene; hydantoin; nifedipine; penicillamine; phenothaiazines; pinacidil; psoralens, verapamil; zidovudine; alpha-glucosylated rutin having at least one of the following rutins: quercetin, isoquercitrin, hesperidin, naringin, and methylhesperidin, and flavonoids and transglycosidated derivatives thereof which are all disdosed in JP 7002677, which is incorporated by reference in its entirety herein; and mixtures thereof.

Preferred hair loss treatment agents include 6-(1-piperidinyl)-2,4-pyrimidinediamine-3-oxide, N"-cyano-N-(tert-pentyl)-N'-3-pyridinyl-guanidine, finasteride, a retinoid and derivatives thereof, ketoconazole, or mixtures thereof.

Another embodiment of the present invention is directed to a method for removing hair comprising topically applying to skin at a desired area for removing hair the above-described composition, e.g. the combination of non-ionic lipid and vehicle solution, containing an effective amount of a depilatory agent, such as the thioglycolades, e.g. calcium thioglycolate, magnesium thioglycolate, potassium thioglycolate, strontium thioglycolate, and mixtures thereof. In a preferred embodiment, the composition contains, based upon the total weight of the composition, from about 0.001 percent to about 20 percent, and preferably from about 0.01 percent to about 5 percent hair depilatory agent.

Another embodiment of the present invention is directed to a method for inhibiting hair growth comprising topically applying to skin at a desired area for inhibiting hair growth the above-described composition, e.g. the combination of non-ionic lipid and vehicle solution, containing an effective amount of a hair growth inhibiting agent. In a preferred embodiment, the composition contains, based upon the total weight of the composition, from about 0.001 percent to about 20 percent, and preferably from about 0.01 percent to about 5 percent hair growth inhibiting agent.

Examples of benefit agents suitable for use in inhibiting hair growth include: serine proteases such as trypsin, vitamins such as alpha-tocophenol (vitamin E) and derivatives thereof such as tocophenol acetate and tocophenol palmitate; antineoplasitc agents, such as doxorubicin, cyclophosphamide, chlormethine, methotrexate, fluorouracil, vincristine, daunorubicin, bleomycin and hydroxycarbamide; anticoagulants, such as heparin, heparinoids, coumaerins, detran and indandiones; antithyroid drugs, such as iodine, thiouracils and carbimazole; lithium and lithium carbonate; interferons, such as interferon alpha, interferon alpha-2a and inferon alpha-2b; retinoids, such as retinol (vitamin A), isotretinoin: glucocorticoids such as betamethasone, dexamethosone: Antihyperlipidaemic drugs, such as triparanol and clofibrate; thallium; mercury; albendazole; allopurinol; amiodarone; amphetamines; androgens; bromocriptine; butyrophenones; carbamazepine; cholestyramine; cimetidine; clofibrate; danazol; desipramine; dixyrazine; ethambutol; etionamide; fluoxetine; gentamicin, gold salts; hydantoins; ibuprofen; impramine; immunoglobulins; indandiones; indomethacin; intraconazole; levadopa; maprotiline; methysergide; metoprolol; metyrapone; nadolol; nicotinic acid; potassium thiocyanate; propranolol; pyridostimine; salicylates; sulfasalazine; terfenadine; thiamphenicol; thiouracils; trimethadione; troparanol; valproic acid; and mixtures thereof. Preferred hair growth inhibitory agents include serine proteases, retinol, isotretinoin, betamethoisone, alpha-tocophenol and derivatives thereof, or mixtures thereof.

Another preferred embodiment of the present invention is directed to a method for treating acne and for reducing the signs of aging, i.e. wrinkles, fine lines, and other manifestations of photodamage, comprising topically applying to skin at a desired area the above-described composition, e.g. the combination of non-ionic lipid and vehicle solution, containing an anti-acne agent or an anti-aging agent, respectively.

Examples of suitable anti-aging agents include, but are not limited to inorganic sunscreens such as tianium dioxide and zinc oxide; organic sunscreens such as octyl-methyl cinnamates and derivatives thereof; retinoids; vitamins such as vitamin E, vitamin A, vitamin C, vitamin B, and derivatives thereof such as viamin E acetate, vitamin C palmitate, and the like; antioxidants including alpha hydroxy acid such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucopehtonic acid, glucopheptono 1,4-lactone, gluconic acid, gluconolactone, glucuronic acid, glucurronolactone, glycolic acid, isopropyl pyruvate, methyl pyruvate, mucic acid, pyruvia acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, rice, safflower, and mixtures thereof. Preferred anti-aging agents include retinoids, anti-oxidants, alpha-hydroxy acids and beta-hydroxy acid with retinol and tretinoin being most preferred.

Examples of suitable anti-acne agents include, but are not limited to topical retinoids (tretinoin, Isotretinoin, Motretinide, Adapalene, Tazarotene, Azelaic acid, retinol); salicylic acid, benzoyl peroxide; antibiotics such as tetracycline and isomers thereof, erthromycin, and the anti-inflammatory agents such as ibbuprofen, naproxen, hetprofen; botanical extracts such as alnus, amica, artemisia capillaris, asiasarum root, birch, calendula, chamomile, cnidium, comfrey, fennel, galla rhois, hawthrorn, houttuynia, hypericum, jujube, kiwi, licorice, magnolia, olive, peppermint, philodendron, salvia, sasa albomarginata; imidazoles such as ketoconazole and elubiol, and those described in Gollnick, H et al. 196(1) Dermatology Sebaceous Glands, Acne and Related Disorders, 119–157 (1998), which is incorporated by reference herein, and mixtures thereof. Preferred anti-acne agents include retinol, elubiol, antibiotics, and salicylic acid, with retinol and tretinoin being most preferred.

Suitable amounts of anti-aging agents include, based upon the total weight of the composition, from about 0.01 percent to about 10 percent, and preferably from about 0.04 percent to about 5 percent. Suitable amount of anti-acne agents include, based upon the total weight of the composition, from about 0.01 percent to about 10 percent, and preferably from about 0.04 percent to about 5 percent.

Another preferred embodiment of the present invention is directed to a method for depigmenting the skin comprising topically applying to skin at a desired area the above-described composition, e.g., the combination of non-ionic lipid and vehicle solution, containing a depigmentation agent. Suitable amounts of depigmentation agents include, based upon the total weight of the composition, from about 0.01 percent to about 10 percent, and preferably from about 0.04 percent to about 5 percent.

Examples of suitable depigmentation agents include, but are not limited to retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof.

Another preferred embodiment of the present invention is directed to a method for treating the diseases of dandruff, seborrheic dermatitis, and psoriasis and/or the symptoms associated therewith comprising topically applying to skin at a desired area the above-described composition, e.g., the combination of non-ionic lipid and vehicle solution, containing an effective amount of an active agent selected from the group consisting of an anti-dandruff agent, an anti-seborrheic dermatitis agent, an anti-psoriasis agent, and mixtures thereof. Suitable amounts of an anti-dandruff agent, an anti-seborrheic dermatitis agent, and an anti-psoriasis agent include, based upon the total weight of the composition, from about 0.001 percent to about 10 percent, and preferably from about 0.01 percent to about 5 percent.

Examples of suitable anti-dandruff agents, anti-seborrheic dermatitis agents, and anti-psoriasis agents nonexclusively include zinc pyrithione, selenium sulfide, sulfur; sulfonated shale oil; salicylic acid; coal tar; povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin; piroctone olamine (Octopirox); selenium sulfide; ciclopirox olamine; anti-psoriasis agents; vitamin A analogs; corticosteroids and mixtures thereof, with elubiol, ketoconazole, coal tar, salicylic acid, zinc pyrithione, selenium sulfide, hydrocortisone, sulfur, menthol, pramoxine hydrochloride and mixtures thereof being preferred.

In a preferred embodiment, especially with respect to hair growth, the composition of the present invention is substantially free from hydroxypropyl methyl cellulose or other film formers known in the art. By "substantially free" it is meant no more than 0.05% of cellulose or derivatives thereof are present.

With respect to hair growth, we have unexpectedly found that the combination of the non-ionic lipid and the vehicle solution, especially in the absence of a higher molecular weight film former, induces hair growth in about half of the time it took for prior art vehicle solutions containing such film formers to do the same. Moreover, we have particularly found that when minoxidil is the selected pharmacologically active substance, hair growth can be stimulated faster than by application of conventional vehicles such as that commercially available from Upjohn under the tradename ROGAINE™ i.e. minoxidil in a 20:60:20 v/v % polyethylene glycol/ethanol/water transport vehicle.

The invention illustratively disclosed herein suitably maybe practiced in the absence of any component, ingredient, or step which is not specifically disclosed herein. Several examples are set forth below to further illustrate the nature of the invention and the manner of carrying it out. However, the invention should not be considered as being limited to the details thereof. Other compositions of the invention can be prepared in an analogous manner by a person of ordinary skill in the art.

EXAMPLE 1

Preparation of a Propylene Glycol, Ethanol and Water Formulation Containing 2% Minoxidil, with and without an Alpha-hydroxy Acid and Sodium Sulfate 0.4 g of minoxidil, U.S.P./N.F., available from Spectrum Quality Products Products, Inc., Gardena, Calif. was added with stirring into a beaker containing 4 ml of propylene glycol, 12 ml of ethanol, and 4 ml water under ambient conditions to produce a formulation containing 2% (wt/v) minoxidil. This formulation is identical to that which is commercially available from the Upjohn Company, Kalamazoo, Mich. under the tradename, "ROGAINE™".

To obtain a formulation containing an alpha-hydroxy acid (used in Example 12), 360 µl of DL-lactic acid was then added under ambient conditions to the above ROGAINE-type formulation.

To obtain a formulation with both an aipha-hydroxy acid and sodium sulfate (used in Example 12), 0.626 g of sodium sulfate was added under ambient conditions to the above hydroxy acid-containing formulation.

EXAMPLE 2

Preparation of Polyoxvethylene-10 Stearyl Ether Formulation Containing 2% Minoxidil After melting 0.5 g of polyoxyethylene-10-stearyl ether available from ICI Surfactants, Wilmington, Del. under the tradename, "BRIJ 76" in a beaker at 50° C., 10 ml of the minoxidil-containing formulation of Example 1 was added thereto with stirring until the resulting mixture was at ambient temperature in order to produce a formulation containing 2% (wt/v) minoxidil with 5% non-ionic lipids.

EXAMPLE 3

Preparation of Three Nonionic Lipid Formulation Containina 2% Minoxidil 0.225 g of glyceryl dilaurate available from Van Dyk & Company, Inc., Belleville, N.J. under the tradename, "Emulsynt GDL," 0.075 g of cholesterol available from Croda, Inc., New York, N.Y. under the tradename, "Cholesterol NF", and 0.2 g of the polyoxyethylene-10-steral ether of Example 2 were mixed in a beaker at 50° C. until the components were homogeneously melted to yield a 45:15:40 weight percent nonionic lipid mixture.

10 ml of the minoxidil-containing formulation of Example 1 were added to 0.5 g of the resulting non-ionic lipid mixture with stirring until the resultant mixture was at ambient temperature in order to yield a formulation containing 2% minoxidil with 5% non-ionic lipids.

EXAMPLE 4

Preparation of Two Nonionic Lipid Formulation Containing 2% Minoxidil 0.25 g of the glyceryl dilaurate of Example 3 and 0.25 g of the polyoxyethylene-10-steral ether of Example 3 were mixed in a beaker at 50° C. until the components were homogeneously melted to yield a 50:50 weight percent nonionic lipid mixture. 10 ml of the formulation of Example 1 was added thereto with stirring until the resulting mixture was at ambient temperature in order to yield a formulation containing 2% minoxidil with 5% non-ionic lipids.

EXAMPLE 5

Preparation of Glyceryl Dilaurate Formulation Containina 2% Minoxidil

After melting 0.5 g of the glyceryl dilaurate of Example 2 with stirring in a beaker at 50° C., 10 ml of the Formulation of Example 1 were then added with thereto with stirring until the resulting formulation was at ambient temperature in order to yield a formulation containing 2% minoxidil with 5% non-ionic lipids.

EXAMPLE 6

Preparation of Anhydrous, Non-Ionic Lipid Composition With Minoxidil 0.4 g of the minoxidil of Example 1 were added with stirring to a beaker containing a mixture of 2 ml of propylene carbonate available from Arco, Newtown Square, Pa. under the tradename, "Arconate HP", 6 ml of ethanol, 1 ml of polyethylene glycol available from Dow Chemical, Midland, Mich., and 1 ml glycerin available from Henkel Chemical Comapny, Cincinnati, Ohio under the tradename, "Glycerin 916" under ambient conditions to produce a solution containing 2% minoxidil. 0.5 g of the nonionic lipid mixture of Example 3 was then added to 10 ml of the resulting solution under ambient conditions to yield a formulation containing 2% non-ionic lipids.

EXAMPLE 7

Preparation of a Anhydrous, Non-Ionic Lipid-Free Composition With 2% Minoxidil 0.4 g of the minoxidil of Example 1 were added with stirring under ambient conditions into a beaker containing a mixture of 4 ml of propylene carbonate, 12 ml of ethanol, 2 ml of propylene glycol, and 2 ml of glycerin, all of Example 6, in order to yield a non-ionic lipid-free composition containing 2% of minoxidil.

EXAMPLE 8

Preparation of Minoxidil-Free Formulations

Examples 1 through 5 were repeated but with the omission of the minoxidil component. The resulting formulations were identified as follows:
  Control 1 (POE) was the minoxidil-free formulation of example 2;
  Control 2 (GDL/CH/POE) was the minoxidil-free formulation of example 3;

Control 3 (POE/GDL) was the minoxidil-free formulation of example 4; and

Control 4 (GDL) was the minoxidil-free formulation of example 5.

EXAMPLE 9

Comparative Testing: Stimulation of Hair Growth in C3H Mouse Model

100 µl of the 2% minoxidil-containing compositions produced in Examples 1 through 4 and 6 through 8, respectively, were applied via pipette to approximately a 1.5 cm$^2$ section of dorsal skin surface of 3–5 C3H mice available from Charles River Breeding Laboratories, Kingston, N.Y. once per day, 5 days per week for 19 days.

Prior to application of the above-described, respective formulations, the mice were screened for telogen (resting phase in hair growth cycle) skin on day 1 by gently blowing on their fur. The appearance of pink skin evidenced the presence of the telogen phase. After the mice were sedated with an i.p. injection of 100 µl ketamine/xylazine solution, their hair was gently clipped with an electric clipper on their respective dorsal sides.

For positive control purposes, 2 similar C3H mice were shaved then depilated at the shaved dorsal section with a hair removal treatment available from Recklitt & Colman Inc, Wayne N.J. under the tradename, "Neet." For negative control purposes, 2 similar C3H mice were left untreated after the shaving.

The mice were observed for hair growth stimulation/inhibition during the dosing period, which was concluded on the 19th day post-shaving due to the appearance of hair growth in the dorsal section of the mice treated with the composition of Example 2. The amount of hair growth is further evidenced in the representations of the dorsal sections illustrated in FIG. 1(A) through FIG. 1(L).

Figure 1B:
FIG. 1(B) is a representation of the dorsal view of the skin of C3H mice taken 19 days after topical application of the formulation comprised of polyoxyethylene-10 stearyl ether and 2% minoxidil of Example 2 thereto, and the corresponding histological view associated therewith.
Figure 1B:
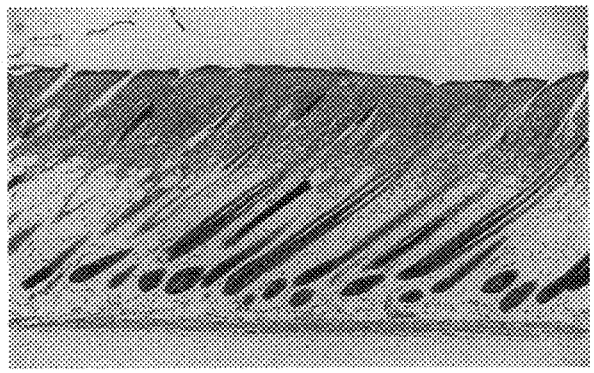
Figure 1C:
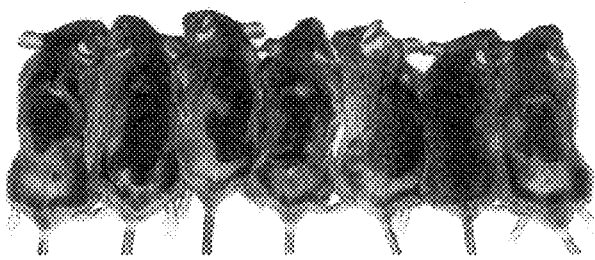
FIG. 1(C) is a representation of the dorsal view of the skin of C3H mice taken 19 days after topical application of the formulation comprised of glyceryl dilaurate, cholesterol, polyoxyethylene-10-stearyl ether and 2% minoxidil of Example 3 thereto, and the corresponding histological view associated therewith.
Figure 1C:
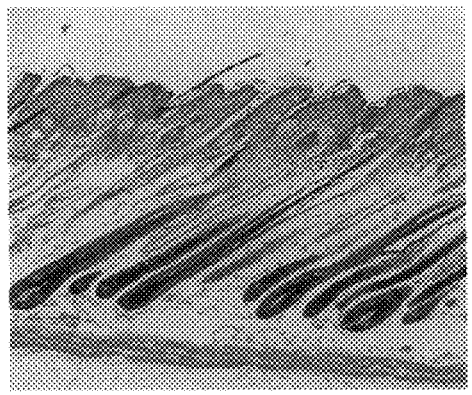
Figure 1D:
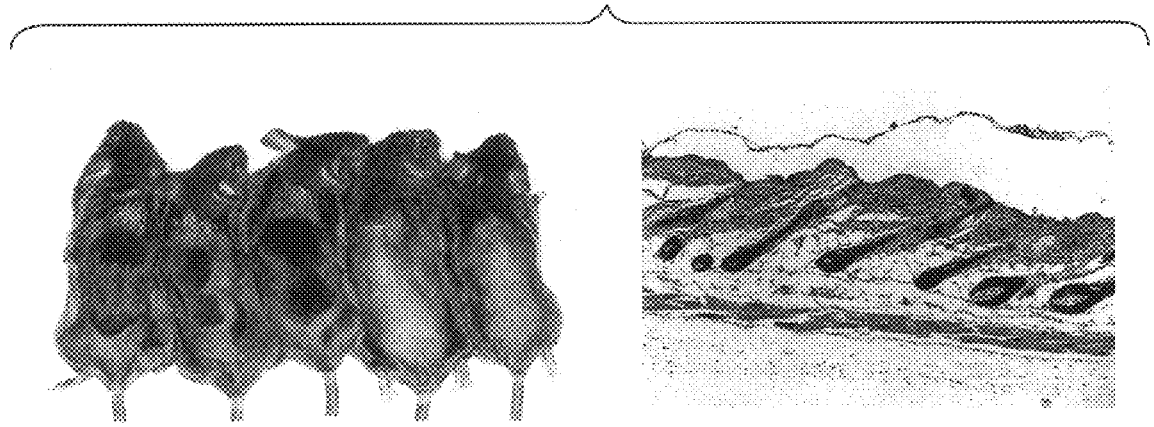
FIG. 1(D) is a representation of the dorsal view of the skin of C3H mice taken 19 days after topical application of the formulation comprised of glyceryl dilaurate, polyoxyethylene-10-stearyl ether and 2% minoxidil solution of Example 4 thereto, and the corresponding histological view associated therewith.
Figure 1E:
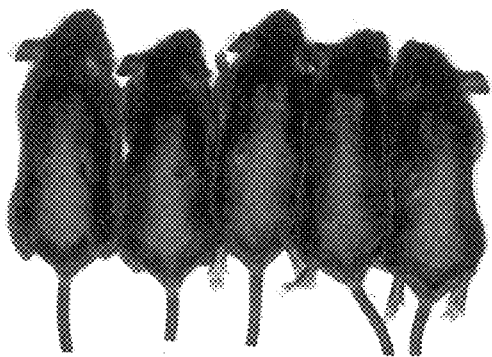
FIG. 1(E) is a representation of the dorsal view of the skin of C3H mice taken 19 days after topical application of the formulation comprised of an anhydrous solution containing glyceryl dilaurate, cholesterol, polyoxyethylene-10-stearyl ether and 2% minoxidil of Example 7 thereto.
Figure 1F:
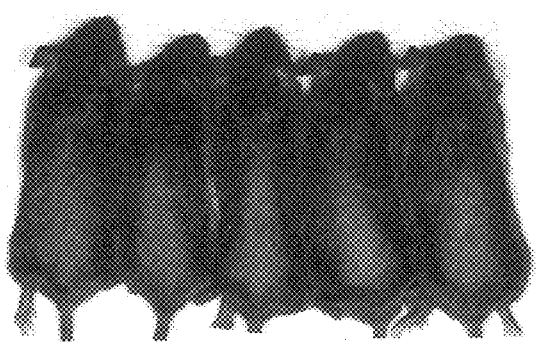
FIG. 1(F) is a representation of the dorsal view of the skin of C3H mice taken 19 days after topical application of the formulation comprised of an anhydrous solution containing 2% minoxidil (without nonionic lipids) of Example 6 thereto.
Figure 1G:
FIG. 1(G) is a representation of the dorsal view of the skin of C3H mice taken 19 days after topical application of the minoxidil-free formulation comprised of the minoxidil-free formulation containing polyoxyethylene-10 stearyl ether of Example 8, Control #1 thereto.
Figure 1H:
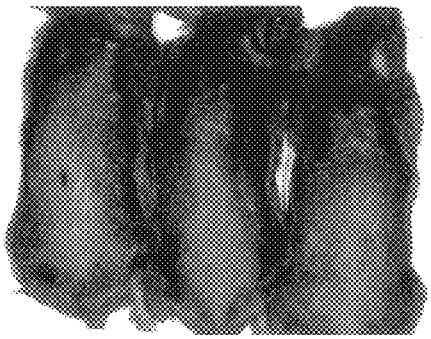
FIG. 1(H) is a representation of the dorsal view of the skin of C3H mice taken 19 days after topical application of the minoxidil-free formulation containing glyceryl dilaurate, cholesterol, polyoxyethylene-10-stearyl ether of Example 8, Control #2 thereto.
Figure 1I:
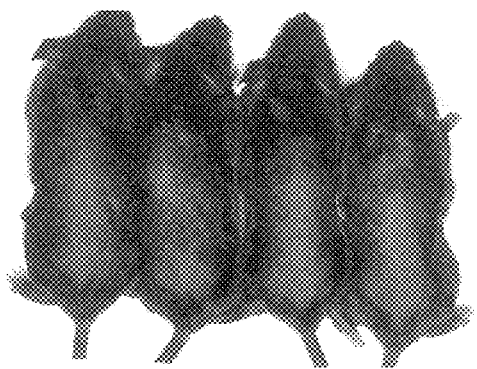
FIG. 1(I) is a representation of the dorsal view of the skin of C3H mice taken 19 days after topical application of the minoxidil-free formulation containing glyceryl dilaurate and polyoxyethylene-10-stearyl ether of Example 8, Control #3 thereto.
Figure 1J:
FIG. 1(J) is a representation of the dorsal view of the skin of C3H mice taken 19 days after topical application of the minoxidil-free formulation containing glyceryl dilaurate of Example 8, Control #4 thereto.
Figure 1K:
FIG. 1(K) is a representation of the dorsal view of the skin of C3H mice taken 19 days after shaving without subsequent treatment (Negative Control of Example 9), and histology corresponding therewith.
Figure 1K:
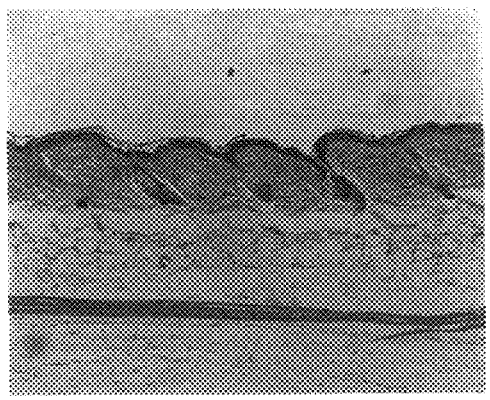
Figure 1L:
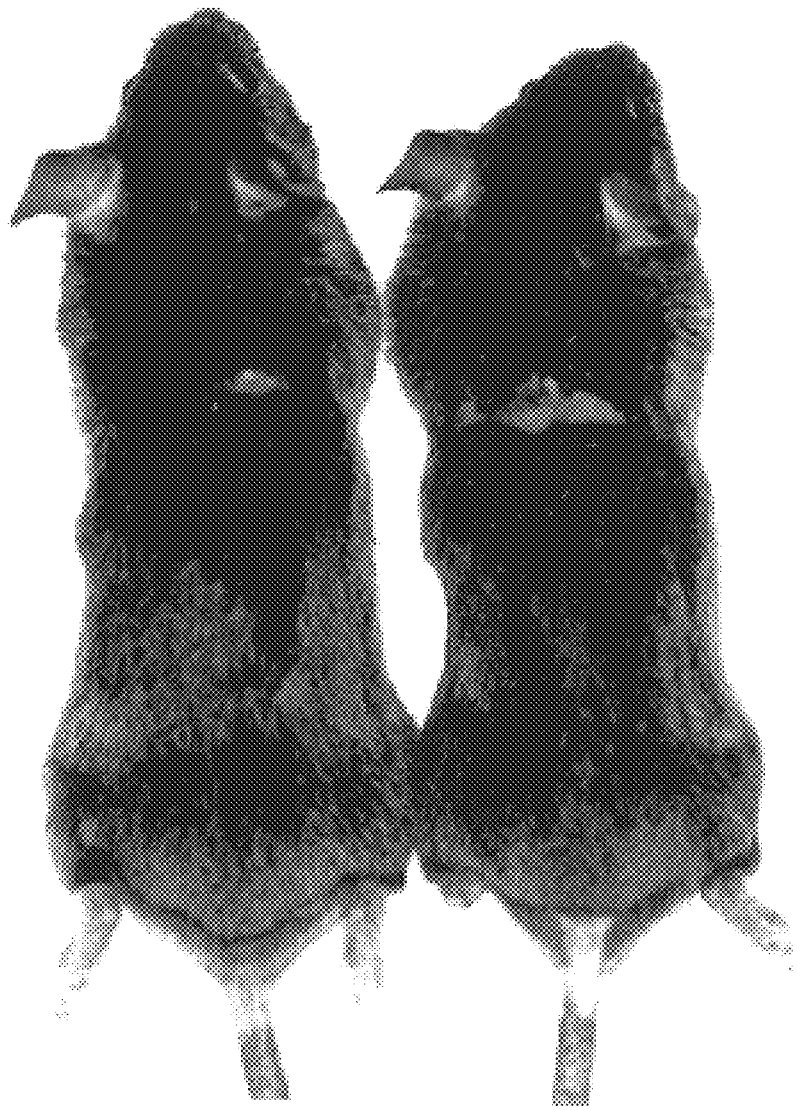
FIG. 1(L) is a representation of the dorsal view of the skin of C3H mice taken 19 days after topical application of a Neet hair removal depilatory cream thereto (Positive Control of Example 9).

As shown in FIG. 1(B), the mice treated with the composition of Example 2 possessed a greater amount of hair growth in comparison to the mice treated with the ROGAINE™ treatment (see FIG. 1(A)), or the mice in the control groups (see FIGS. 1(G)–1(L)).

As further evidenced in the histological representations of FIG. 1(A) through FIG. 1(D) and FIG. 1(K), it is evident that the mice treated with the enhanced vehicles from Examples 2–4 demonstrated long, anagen follicles, i.e. follicles in the growth state of the hair growth cycle, whereas the mice treated with the Rogaine formulation demonstrated follicles only in the telogen state. The untreated mice in FIG. 1(K) similarly demonstrated follicles in only the telogen state. This indicated that, from a follicullar perspective, the formulations produced in Examples 2–4 were superior in enhancing hair growth in contrast to the Rogaine formulations, which did not appear to stimulate hair growth at all.

This Example showed that the composition of the present invention, which contained a vehicle solution combined with a non-ionic lipid, stimulated more hair growth at a considerable faster rate in comparison to amount and rate of hair growth stimulated by the ROGAINE treatment.

EXAMPLE 10

Preparation of a Propylene Glycol, Ethanol and Water Formulation Containing 5% Minoxidil, both with and without Sodium Sulfate 0.5 g of the minoxidil of Example 1 were mixed with stirring into a beaker containing a mixture of 2 ml of propylene glycol, 6 ml of ethanol, and 2 ml water under ambient conditions to produce a formulation containing 5% minoxidil. This formulation is identical to that which is commercially available from the Upjohn Company, Kalamazoo, Mich. under the tradename, "ROGAINE 5%™"

For sodium sulfate-containing formulations (as used in Example 12), 0.313 g of sodium sulfate was then added thereto.

EXAMPLE 11

Preparation of a Novel Polyoxyethylene-10 Stearyl Ether, Alpha-hydroxy Acid Formulation with 5% Minoxidil, both with and without 1.4% Sodium Sulfate After melting 0.5 g of the polyoxyethylene-10-steral ether of Example 2 in a beaker at 50° C., 10 ml of the minoxidil-containing formulation of Example 1 and 360 µl of DL-iactic acid were then added thereto with mixing until the resulting mixture reached ambient temperature. The resulting mixture contained 2% minoxidil with 5% non-ionic lipids and a alpha-hydroxy acid. A few drops of 0.1M hydrochloric acid was then added thereto in order to adjust the pH of the resulting composition to about 4.6.

In sodium sulfate-containing formulations, 0.26 g of sodium sulfate was added to the above resulting mixture before the addition of the pH-adjusting acid thereto.

EXAMPLE 12

Comparative Testing: Stimulation of Hair Growth in a More Resistant C57 Mouse Model 100 µl of the formulations of Example 1, 10, and 11 were applied via pipette to about a 4 cm$^2$ section of dorsal skin surface of 3–5 C57B116 female, 7 week old mice available from is Charles River Breeding Laboratories, Kingston, N.Y., respectively, once a day, 5 days per week for 25 days.

For positive control purposes, 5 similar C57BI/6 mice were shaved in the same manner then depilated at the same dorsal section with the NEET hair removal treatment of Example 8. For negative control purposes, 5 similar C57BI/6 mice were left untreated after the shaving.

Prior to application of the above-described, respective formulations, the mice were screened for telogen (resting phase in hair growth cycle) skin on day 1 by gently blowing on their fur. The appearance of pink skin evidenced the presence of the telogen phase. After the mice were sedated with an i.p. injection of 100 µl ketamine/xylazine solution, their hair was gently clipped with an electric clipper on their respective dorsal sides.

The mice were observed for hair growth stimulation/inhibition during the dosing period. Every two days during the dosing period the status of the hair and the skin were classified and recorded as "full coat," "spotty hair," "black skin" (little or no hair) and "no hair." These number of days in each hair growth status were averaged in each dosing group and the standard deviation was determined within each dosing group. The results of this Example are shown in Table 1.

TABLE 1

| Formulation | Black Skin | Spotty Hair | Full Coat |
|---|---|---|---|
| Rogaine 2% {Example 1} | 18 ± 2* | 22.0 ± 0.0 | >26 |
| Rogaine 2% + Lactic acid {Example 1} | 16.4 ± 5.2 | >22 | >26 |
| Rogaine 2% + Lactic acid + sodium sulfate {Example 1} | 14.0 ± 3.7 | >18 | >23 |
| Rogaine 5% {Example 10} | 10.5 ± 3.8 | 12.0 ± 4.0 | 15.5 ± 3.0 |
| Rogaine 5% + sodium sulfate {Example 10} | 10.0 ± 2.3 | 12.5 ± 2.5 | 18.8 ± 5.4 |
| Untreated {Example 12} | >26 | >26 | >26 |
| 2% Minoxidil + lipid + lactic acid {Example 11} | 8.0 ± 1.5 | 11.5 ± 1.9 | 13.5 ± 1.9 |
| 2% Minoxidil + lipid + lactic acid + sodium sulfate {Example 11} | 7.6 ± 0.5 | 9.2 ± 1.8 | 13.2 ± 1.8 |
| Neet depilatory {Example 12} | 9.3 ± 1.2 | 12.0 ± 0.0 | 15.3 ± 2.3 |

*Expressed in terms of number of days to express condition.

It was observed that the hair and skin of the untreated animals remained in the telogen state for the duration of the dosing period (negative control), while the hair and skin of the depilatory-treated mice started to exhibit melanogenesis after 10–25 days of dosing (positive control).

As shown in Table 1, the formulations that induced the most rapid onset of hair growth were those produced in Example 11, i.e. the combination of 2% minoxidil, polyoxyethylene-10-steral ether, lactic acid, and optional sodium sulfate, with the formulation containing the sodium sulfate being the most preferred.

This Example showed that the formulations of Example 11, which contained only 2% minoxidil in the delivery system of the present invention, outperformed the 5%-minoxidil-containing formulation of Example 10 with respect to speed and quantity of hair growth stimulation due to the addition of the unique delivery system of the present invention that was added thereto.

This Example further showed that the addition of sodium sulfate to the formulations of the present invention also improved the speed and amount of hair growth This Example further showed that the addition of an alpha hydroxy acid ('AHA') to the 2% minoxidil-containing formulations of the present invention (Example 11) also resulted in a faster onset of thicker hair growth relative to that achieved by the 2% -minoxidil formulation in the ROGAINE vehicle (Examples 1), regardless if the latter optionally contained lactic acid and sodium sulfate.

EXAMPLE 13

Preparation of Lipid Formulation Containing Minoxidil and Ketoconazole, both with and without Sodium Sulfate 0.4 g of the minoxidil of Example 1 and 0.4 g ketoconazole available from Janssen Pharmaceutica N.V., Beerse, Belgium, were added with stirring at ambient temperature and pressure into a beaker containing 4 ml of propylene glycol, 12 ml of ethanol, and 4 ml water to produce a 2% minoxidil/ketoconazole-containing solution.

0.5 g of the polyoxyethylene-10-steral ether of Example 2 was melted in a beaker at 50° C. and added into 10 ml of the 2% minoxidil/ketoconazole-containing solution with stirring until the resulting mixture reached ambient temperature in order to produce a composition containing 2% minoxidil, 2% ketoconazole, and 5% non-ionic lipids.

These steps were repeated but with the addition of 0.28 g sodium sulfate into the mixture of water, ethanol, and propylene glycol in order to result in a composition containing 2% minoxidil, 2% ketoconazole, 5% non-ionic lipids, and 1.4% sodium sulfate.

EXAMPLE 14

Preparation of Ketoconazole-Lipid Formulation 0.5 g of the polyoxyethylene-10-steral ether of Example 2 were melted in a beaker at 50° C.

0.4 g of the ketoconazole of Example 13 were added with stirring into a beaker containing a mixture of 4 ml of propylene glycol, 12 ml of ethanol, and 4 ml water at ambient temperature and pressure to yield a ketoconazole-containing vehicle solution.

10 ml of the ketoconazole-containing vehicle solution were added into the melted ether at 50° C. with stirring until the resulting mixture reached to room temperature in order to yield a composition containing 2% ketoconazole with 5% non-ionic lipids.

EXAMPLE 15

Preparation of Minoxidil and Finasteride Lipid Formulation 0.5 g of the polyoxyethylene-10-steral ether of Example 2 was melted in a beaker at 50° C.

0.4 g of the minoxidil of Example 1 and 0.4 g of finasteride available from Sigma Chemical Company, St. Louis, Mo. were added with stirring at ambient temperature into a beaker containing a mixture of 4 ml of propylene glycol, 12 ml of ethanol, and 4 ml water to produce a vehicle solution containing finasteride and 2% minoxidil.

10 ml of the vehicle solution were then added with stirring into the melted non-ionic lipid melt at 50° C. and then cooled to room temperature to yield a composition containing 2% minoxidil and 2% finasteride with 5% non-ionic lipids.

EXAMPLE 16

Preparation of Minoxidil-free, Finasteride —Lipid Formulation 0.5 g of the polyoxyethylene-10-steral ether of Example 2 was melted in a beaker at 50° C.

0.4 g of the finasteride of Example 15 were added with stirring at ambient temperature into a beaker containing mixture of 4 ml of propylene glycol, 12 ml of ethanol, and 4 ml water to produce a finasteride-containing vehicle solution.

10 ml of the vehicle solution was then added with stirring into the melted non-ionic lipid melt at 50° C. and then cooled to room temperature to yield a minoxidil-free composition containing 2% finasteride with 5% non-ionic lipids.

EXAMPLE 17

Preparation of Minoxidil-lipid Formulation with Hydroxypropyl Methyl Cellulose 0.5 g of polyoxyethylene-10-stearyl ether of Example 2 were melted in a beaker at 50° C. 10 ml of the minoxidil-containing formulation of Example 1 was added thereto with stirring at constant temperature. 0.05 g of a hydroxypropylmethylcellulose film former available from Hercules, Inc, Wilmington, Del. under the tradename, "Klucel HF" was then added thereto with stirring at constant temperature to produce a composition containing 2% minoxidil with 5% non-ionic lipids and 0.5% hydroxypropylmethylcellulose.

EXAMPLE 18

Comparative Testing: Stimulation of Hair Growth

100 µl of the 2% minoxidil-containing compositions in Examples 1, 2, 10, 12–16 were independently applied via pipette to the entire dorsal skin surface of 3–5 C57BI/6 female, 7 week old mice available from Charles River Breeding Laboratories, Kingston, N.Y., respectively, once per day, 5 days per week for 25 days.

For positive control purposes, 5 similar C57 mice were shaved in the same manner then depilated at the same dorsal section with the Neet hair removal treatment of Example 8. For negative control purposes, 5 similar C57 mice were left untreated after the shaving.

The animals were observed for hair growth stimulafion-linhibition during the dosing period in accordance with the procedure set forth in Example 12. The results of our observations are set forth below in Table 2:

TABLE 2

| Formulation | Black Skin | Spotty Hair | Full Coat |
|---|---|---|---|
| ROGAINE 2% (Example 1) | 25.6 ± 0.5* | >26 | >26 |
| ROGAINE 5% (Example 10) | 11.5 ± 1.0 | 17.0 ± 4.8 | 23.0 ± 2.4 |
| Untreated | >26 | >26 | >26 |
| ROGAINE 2% in cellulose (Example 16) | 21.2 ± 3.0 | 24.0 ± 1.9 | 25.8 ± 0.4 |
| 2% Minoxidil in lipid (Example 2) | 9.2 ± 1.8 | 12.8 ± 1.1 | 16.0 ± 1.4 |
| 2% Minoxidil in lipid with 2% Ketoconazole + 1.4% Sodium Sulfate (Example 13) | 9.6 ± 2.2 | 12.8 ± 1.8 | 16.4 ± 2.6 |
| 2% Minoxidil in lipid with 2% Ketoconazole (Example 13) | 9.6 ± 1.7 | 12.4 ± 2.6 | 16.0 ± 3.2 |
| MINOXIDIL-FREE, 2% Ketoconazole-lipid (Example 14) | 24.0 ± 2.8 | >26 | >26 |
| 2% Minoxidil in lipid with 2% Finasteride (Ex. 15) | 9.2 ± 1.8 | 11.0 ± 1.1 | 12.5 ± 1.8 |
| MINOXIDIL-FREE, 2% Finasteride in lipid (Ex. 16) | 14.0 ± 3.7 | 18.0 ± 3.2 | 25.0 ± 0.0 |
| Neet (Example 12-positive control) | 12.0 ± 2.0 | 14.7 ± 1.2 | 18.7 ± 1.2 |

*Expressed in terms of number of days to express condition.

As shown in Table 2, the formulations that contained the minoxidil in the novel non-ionic lipid formulation demonstrated the most rapid onset of hair growth and performed substantially better in stimulating hair growth than the ROGAINE formulations containing as much as 5% minoxidil.

We further found that the formulations containing the minoxidil and non-ionic lipid combination were superior in stimulating hair growth relative to the 2% ROGAINE formulation with cellulose of Example 16.

This Examples shows that, with respect to stmulating the onset of hair growth, the minoxidil-lipid formulations of the present invention are superior to the known minoxidil Rogaine formulations that contain greater than two times the amount of minoxidil as well as those minoxidil-lipid formulations containing cellulose film formers.

EXAMPLE 19

Preparation of 2% Minoxidil Formulation containing Two Nonionic Lipids 0.25 g of the polyoxyethylene-10-stearyl ether of Example 2 and 0.25 g of polyoxyethylene-9-lauryl ether available from Heterene, Inc., Paterson, N.J. under the tradename, "Laureth-9" were melted in a beaker at 50° C. 10 ml of the minoxidil-containing formulation of Example 1 were added into the non-ionic lipid mixture at 50° C. with stirring until the resultant composition was at ambient temperature in order to yield a composition containing 2% minoxidil with 5% non-ionic lipids.

EXAMPLE 20

Delivery of Minoxidil into the Pilosebaceous Units: Determined by a Hamster Ear Model Because the hamster ear pilosebaceous units are shown to have anatomical and physiological similarities to those of human sebaceous glands, Plewig, G. et al., "*Hamster ear model for sebaceous glands*," 68: J. Invest Dermatol. 171–176 (1977) and Matias, J. R. et al., "*The hamster ear sebaceous glands. I. Examination of the regional variation by stripping skin planarimetry.*" 81: J. Invest. Dermatol. 43–46 (1983), hamsters are known for providing an effective model for estimating the extent and rate of deposition of active agents into pilosebaceous units.

A trace amount of radioactive (3H) minoxidil, purchased from American Radiolabeled Chemicals, Inc, St. Louis Mo., was added to each formulation from Examples 1, 2, and 19, respectively, to produce radiolabeled formulations.

25 µl of cold (without radioactivity) formulation from each respective example was applied twice a day for one day to the ventral ear of 3 male, 10 week old, golden Syrian hamsters obtained from Charles Rivers Breeding Laboratories, Kingston, N.Y. i.e., six ears per formulation. These mice were housed in separate cages under a 14 hours light and 10 hours dark cycle for two weeks before use in order to maximize androgen-dependent sebaceous gland activity and thus control their size.

At 15 hours after the second application of each respective formulation and after anesthetizing the mice, 25 µL of the radiolabeled minoxidil formulation was similarly applied to each ear. After 4 hours, the ears were processed according to Niemiec, S. M. et. al., "*Influence of nonionic liposomal composition on topical delivery of peptide drugs into pilosebaceous unfts: An in-vivo study using the hamster ear model*" 12 Pharm. Research, 1184–1188 (1995), which is incorporated by reference herein. The results of this Example are shown below in Table 3:

TABLE 3

| | Distribution of Minoxidil | | |
|---|---|---|---|
| Ear Strata (% radiolabelled formulation (µg) in strata) | 2% Minoxidil in Rogaine solution {Example 1} | 2% Minoxidil in one nonionic lipid formulation {Example 2} | 2% Minoxidil in two nonionic lipids {Example 19} |
| Sebaceous Glands | 0.04 ± 0.01 (0.18 ± 0.04) | 0.12 ± 0.02 (0.57 ± 0.08) | 0.13 ± 0.05 (0.60 ± 0.19) |
| Ventral Dermis | 0.0 ± 0.0 | 0.02 ± 0.0 | 0.02 ± 0.0 |
| Cartilage | 0.02 ± 0.01 | 0.05 ± 0.01 | 0.05 ± 0.02 |
| Dorsal Ear | 0.01 ± 0.0 | 0.04 ± 0.01 | 0.04 ± 0.01 |

It is evident from Table 3 that the formulations containing the novel delivery systems of the present invention having either one or two non-ionic lipids delivered over three times the amount of minoxidil into the sebaceous glands relative to the amount delivered by the formulations containing the known Rogaine vehicle solution.

This Example shows that the non-ionic lipid-containing vehicles of the present invention are more effective in delivering the active agents into the sebaceous glands and hair follicles than vehicles known in the art.

EXAMPLE 21

Preparation of Hair Growth Formulations

After melting the lipids set forth below in a beaker at 50° C., the remaining ingredients, except for the active agents, are added with stirring thereto at constant temperature. After the mixture is homogeneous, the hair growth agents are added thereto with stirring at constant temperature. When these formulations are topically applied to the scalp, the rate of hair growth is improved.

TABLE 4

| | Concentration (weight %) | | | |
|---|---|---|---|---|
| Components | Ex 1 | Ex 2 | Ex 3 | Ranges Ex 4 |
| Minoxidil | 2 | 2 | 2 | 0–10 |
| Ketoconazole | 0 | 2 | 2 | 0–5 |
| Finasteride | 0 | 0 | 2 | 0–5 |
| Ethanol | 60 | 40 | 20 | 20–80 |
| 1,3-butylene glycol | 12.5 | 20 | 20 | 5–20 |
| Propylene Glycol | 12.5 | 20 | 20 | 1–40 |
| Glyceryl Distearate* | 2 | 0 | 0 | 0.0–5 |
| Cholesterol | 0 | 0 | 0.5 | 0–1 |
| Glyceryl Dilaurate | 0 | 0 | 1 | 0–5 |
| Polyoxyethylene-9-laurayl ether (Laureth-9) | 2 | 0 | 1 | 0–5 |
| Polyoxyethylene-10-stearyl ether (BRIG 76) | 1 | 5 | 2.5 | 0–5 |
| Fragrance | 0.25 | 0.25 | 0.25 | 0–0.5 |
| Polyoxypropylene-polyoxyethylene block polymers (Pluronic F-127)** | 0 | 5 | 0 | 1–20 |
| Polyacrylamine, Laueth-7, and C13–14 Isoparaffin (Sepigel 305)*** | 0 | 0 | 3 | 0–5 |
| Water | q.s. to 100% | q.s. to 100% | q.s. to 100% | q.s. to 100% |

*available from Armak Company, McCook, IL, under the tradename, "Kessco GDS 386F."
**available from BASF Wyandotte Corp., Parsippany, NJ, under the tradename "Pluronic F-127"
***available from Seppic Inc., Fairfield, NJ, under the tradename, "Sepigel-305"

EXAMPLE 22

Preparation of Anti-aging Agent-Lipid Formulations

The below formulations are prepared in accordance with the procedure set forth in Example 21. When these formulations are applied to the skin, the symptoms of aging are reduced.

TABLE 5

| | Concentration (weight %) | | | |
|---|---|---|---|---|
| Components | Ex 1 | Ex 2 | Ex 3 | Ranges Ex 4 |
| Retinol* | 0.15 | 0.15 | 0.15 | 0–2 |
| Glycolic acid** | 0 | 3 | 0 | 0–10 |
| Vitamin E*** | 0 | 0 | 1 | 0–5 |
| Ethanol | 60 | 40 | 20 | 20–80 |
| 1,3-butylene glycol | 12.5 | 20 | 20 | 5–20 |
| Propylene Glycol | 12.5 | 20 | 20 | 1–40 |
| Glyceryl Distearate | 2 | 0 | 0 | 0.0–5 |
| Cholesterol | 0 | 0 | 0.5 | 0–1 |

TABLE 5-continued

| | Concentration (weight %) | | | |
|---|---|---|---|---|
| Components | Ex 1 | Ex 2 | Ex 3 | Ranges Ex 4 |
| Glyceryl Dilaurate | 0 | 0 | 1 | 0–5 |
| Laureth-9 | 2 | 0 | 1 | 0–5 |
| Polyoxyethylene-10-stearyl ether (Brig 76) | 1 | 5 | 2.5 | 0–5 |
| Fragrance | 0.25 | 0.25 | 0.25 | 0–0.5 |
| Polyacrylamine, Laueth-7, and C13–14 Isoparaffin (Sepigel 305) | 0 | 0 | 3 | 0–5 |
| Polyoxypropylene-polyoxyethylene block polymers (Pluronic F-127) | 0 | 5 | 0 | 1–20 |
| water | q.s. to 100% | q.s. to 100% | q.s. to 100% | q.s. to 100% |

*available from BASF Corp., Parsippany NJ under the tradename, "Retinol 50C"
**available from E.I. DuPont de Nemour Company, Inc., Wilmington, DE under the tradename, "GlyPure 70%";
***available from Hoffman-Laroche, Inc., Nutley, NJ

EXAMPLE 23

Anti-acne Agent—Lipid Formulations

The below formulations are prepared in accordance with the procedure set forth in Example 22. When these formulations are topically applied to the skin, the symptoms of acne are improved.

TABLE 6

| | Concentration (weight %) | | | |
|---|---|---|---|---|
| Components | Ex 1 | Ex 2 | Ex 3 | Ranges Ex 4 |
| Retinol | 0.05 | 0 | 0.05 | 0–2 |
| Benzoyl Peroxide* | 0 | 2 | 2 | 0–10 |
| Elubiol** | 0.1 | 0.1 | 0.1 | 0.001–2 |
| Salicylic acid*** | 2 | 0 | 0 | 0–10 |
| Ethanol | 60 | 40 | 20 | 20–80 |
| 1,3-butylene glycol | 12.5 | 20 | 20 | 5–20 |
| Propylene Glycol | 12.5 | 20 | 20 | 1–40 |
| Glyceryl Distearate | 2 | 0 | 0 | 0.0–5 |
| Cholesterol | 0 | 0 | 0.5 | 0–1 |
| Glyceryl Dilaurate | 0 | 0 | 1 | 0–5 |
| Laureth-9 | 2 | 0 | 1 | 0–5 |
| Polyoxyethylene-10-stearyl ether (Brig 76) | 1 | 5 | 2.5 | 0–5 |
| Fragrance | 0.25 | 0.25 | 0.25 | 0–0.5 |
| Polyacrylamine, Laueth-7, and C13–14 Isoparaffin (Sepigel 305) | 0 | 0 | 3 | 0–5 |
| Polyoxypropylene-polyoxyethylene block polymers (Pluronic F-127) | 0 | 5 | 0 | 1–20 |
| Water | q.s. to 100% | q.s. to 100% | q.s. to 100% | q.s. to 100% |

*available from Alzo Inc., Matawan, NJ
**available from Janssen Pharmaceutica N.V., Beerse, Belgium under the tradename, "Elubiol";
***available from NIPA Laboratories Inc., Great Britain, UK

EXAMPLE 24

Depigmentation Agent—Lipid Formulations

The below formulations are prepared in accordance with the procedure set forth in Example 22. When these formulations are topically applied to the skin, the pigmentation in the skin is reduced.

TABLE 7

| | Concentration (weight %) | | | |
|---|---|---|---|---|
| Components | Ex 1 | Ex 2 | Ex 3 | Ranges Ex 4 |
| Retinol | 0.05 | 0 | 0.05 | 0–2 |
| Kojic acid* | 0 | 1 | 1 | 0–10 |
| Transexamic acid** | 0.05 | 0.05 | 0.05 | 0–5 |
| Hydroquinone*** | 2.0 | 0 | 0 | 0–10 |
| Ethanol | 60 | 40 | 20 | 20–80 |
| 1,3-butylene glycol | 12.5 | 20 | 20 | 5–20 |
| Propylene Glycol | 12.5 | 20 | 20 | 1–40 |
| Glyceryl Distearate | 2 | 0 | 0 | 0.0–5 |
| Cholesterol | 0 | 0 | 0.5 | 0–1 |
| Glyceryl Dilaurate | 0 | 0 | 1 | 0–5 |
| Laureth-9 | 2 | 0 | 1 | 0–5 |
| Polyoxyethylene-10-stearyl ether (Brig 76) | 1 | 5 | 2.5 | 0–5 |
| Fragrance | 0.25 | 0.25 | 0.25 | 0–0.5 |
| Polyacrylamine, Laueth-7, and C13–14 Isoparaffin (Sepigel 305) | 0 | 0 | 3 | 0–5 |
| Polyoxypropylene-polyoxyethylene block polymers (Pluronic F-127) | 0 | 5 | 0 | 1–20 |
| Water | q.s. to 100% | q.s. to 100% | q.s. to 100% | q.s. to 100% |

*available from Sino Lion, New York, NY under the tradename, "Kojic Acid SL";
**available from Sigma Chemical Co., St. Louis, MO
***available from Eastern Company, Kingsport, TN

EXAMPLE 25

Hair Growth Inhibitina Agent—Lipid Formulations

The below formulations are prepared in accordance with the procedure set forth in Example 22. When these formulations are topically applied to the skin, hair growth is inhibited.

TABLE 8

| | Concentration (weight %) | | | |
|---|---|---|---|---|
| Components | Ex 1 | Ex 2 | Ex 3 | Ranges Ex 4 |
| Retinol | 0.15 | 0.15 | 0.15 | 0–2 |
| Betamethasone* | 0 | 0 | 0.05 | 0–1 |
| Cimetidine* | 0 | 2 | 2 | 0–5 |
| Ethanol | 60 | 40 | 20 | 20–80 |
| 1,3-butylene glycol | 12.5 | 20 | 20 | 5–20 |
| Propylene Glycol | 12.5 | 20 | 20 | 1–40 |
| Glyceryl Distearate | 2 | 0 | 0 | 0.0–5 |
| Cholesterol | 0 | 0 | 0.5 | 0–1 |
| Glyceryl Dilaurate | 0 | 0 | 1 | 0–5 |
| Laureth-9 | 2 | 0 | 1 | 0–5 |
| Polyoxyethylene-10-stearyl ether (Brig 76) | 1 | 5 | 2.5 | 0–5 |
| Fragrance | 0.25 | 0.25 | 0.25 | 0–0.5 |
| Polyacrylamine, Laueth-7, and C13–14 Isoparaffin (Sepigel 305) | 0 | 0 | 3 | 0–5 |
| Polyoxypropylene-polyoxyethylene block polymers (Pluronic F-127) | 0 | 5 | 0 | 1–20 |

TABLE 8-continued

| | Concentration (weight %) | | | |
|---|---|---|---|---|
| Components | Ex 1 | Ex 2 | Ex 3 | Ranges Ex 4 |
| water | q.s. to 100% | q.s. to 100% | q.s. to 100% | q.s. to 100% |

*available from Sigma Chemical Co., St. Louis, MO

EXAMPLE 26

Preparation of Elubial Gels

Both 1 g of Pemulen TR1 (Acrylates/C10–30 Alkyl Acrylate Crosspolymer, BF Goodrich Specialty Chemicals, Cleveland, Ohio) and 0.2 g of Natrosol 250 HX (Hydroxyethylcellulose, Hercules, Wilmington, Del.) were suspended in 50 ml of distilled water. The resulting suspension was stirred at room temperature until a homogeneous gel was formed ("Phase 1"). Next, 1 g of panthenol (BASF Co, Parasipany, N.J.), 1 g of Vitamin E acetate (BASF Co., Parasipany, N.J.), 0.1 g of elubiol (Janssen Research Foundation, Beerse, Belgium), 12 g of ethanol, 3 g of Propylene Glycol (Spectrum Quality Products, Inc, Gardena, Calif.), 0.5 g of famesol (Roche Vitamins & Fine Chemicals, Nutley, N.J.), 2 g of hamamelis virginiana (Florasynth, Milan, Italy), 0.25 g of bisabolol (BASF Co, Parasipany, N.J.), 0.25 g of phytantriol (Roche Vitamins & Fine Chemicals, Nutley, N.J.), and 4 g of Arlamol HD (isohexadecane, ICI surfactant, Wilmington, Del.) were all mixed together to form Phase 2. Next, 50 g of Phase 1 was mixed with 24.1 g of Phase 2 to form Phase 3. Then, 12 g of Propylene Glycol, 5 g of isopropyl myristate (Spectrum Quality Products, Inc, Gardena, Calif.), 2 g of ethanol, and 6 g of distilled water were mixed into Phase 3 to form Phase 4. Then, 1.5 ml of 20% NaOH was added to Phase 4 under stirring to form a gel. Lastly, 0.35 ml of Tween 20 (polysorbate 20, ICI surfactant, Wilmington, Del.) was added and mixed well into 40 g of the gel.

EXAMPLE 27

Preparation of Elubial Gels

The below formulations are prepared in accordance with the procedure set forth in Example 26. When these formulations are topically applied to the skin, the sebum production is inhibited and the symptoms of acne are improved.

TABLE 9

| | Concentration (%) | | | |
|---|---|---|---|---|
| Component | EX 1 | EX 2 | EX 3 | Ranges EX 4 |
| Hydroxyethylcellulose | 0.2 | 0.2 | 0.2 | 0–2 |
| Acrylates/C10-30 Alkyl Acrylate Crosspolymer | 1 | 1 | 1 | 0.2–3 |
| Etahnol | 12 | 12 | 12 | 5–30 |
| Elubiol | 0.1 | 0.1 | 0.1 | 0.02–1 |
| Famesol | 0.5 | 0.5 | 0.5 | 0–1 |
| Propylene Glycol | 3 | 12 | 12 | 1–20 |
| Panthenol | 1.3 | 1.3 | 1.3 | 0–5 |
| Hamamelis Virginiana | 2 | 2 | 2 | 0–5 |
| Fragrance | 0.5 | 0.5 | 0.5 | 0–1 |
| Isohexadecane | 4 | 4 | 4 | 0–10 |
| Tocopheryl Acetate | 1 | 1 | 1 | 0–2 |
| Bisabolol | 0.25 | 0.25 | 0.25 | 0–1 |
| Phytantriol | 0.25 | 0.25 | 0.25 | 0–2 |

TABLE 9-continued

| | Concentration (%) | | | |
|---|---|---|---|---|
| Component | EX 1 | EX 2 | EX 3 | Ranges EX 4 |
| Sodium Hydroxide | 0.35 | 0.35 | 0.35 | 0.2–0.5 |
| Polysorbate 20 | 1 | | 1 | 0–3 |
| Isopropyl myristate | | 5 | 5 | 0–15 |
| Polyoxyethylene-10-stearyl ether | 2 | | 1 | 0–5 |
| Polyoxyethylene-2-cettyl ether | | | 1 | 0–5 |
| DI Water | q.s. to 100% | q.s. to 100% | q.s. to 100% | q.s. to 100% |

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method for enhancing the topical application of a benefit agent which comprises topically administering to a human or animal a micellar composition comprising, based upon the total weight of the composition:
   A. from about 1 percent to about 10 percent of a nonionic lipid selected from the group consisting of:
      i. glyceryl monoesters having a fatty acid chain containing from about 3 to about 50 carbon atoms;
      ii. glyceryl diesters having a fatty acid chain containing from about 5 carbon atoms to about 25 carbon atoms;
      iii. alkoxylated alcohols alkoxylated with ethylene oxide or propylene oxide;
      iv. alkoxylated alkyl phenols alkoxylated with ethylene oxide or propylene oxide;
      v. alkoxylated acids alkoxylated with ethylene oxide or propylene oxide;
      vi. alkoxylated amides alkoxylated with ethylene oxide or propylene oxide;
      vii. alkoxylated sugar derivatives alkoxylated with ethylene oxide or propylene oxide;
      viii. alkoxylated derivatives of natural oils or waxes alkoxylated with ethylene oxide or propylene oxide;
      ix. polyoxyethylene fatty ethers having a fatty acid chain containing from about 10 carbon atoms to about 18 carbon atoms;
      x. steroids;
      xi. fatty acid esters of alcohols where the fatty acid is straight or branched chain having from about 10 carbon atoms to about 20 carbon atoms and the alcohol is straight or branched chain having 1 to 10 carbon atoms; and
      xii. mixtures thereof;
   B. from about 74 percent to about 98 percent of a vehicle comprised of:
      1) a first vehicle component comprised of water; and
      2) a second vehicle component comprised of an alcohol, a polyol, or mixtures thereof; and
   C. an effective amount of the skin or hair benefit agent, wherein said micelle is comprised of said nonionic lipid and said second vehicle component.

2. A method for treating hair loss comprising topically administering to a human or animal at a desired area for treating hair loss a micellar composition comprising, based upon the total weight of the composition:
   A. from about 1 percent to about 10 percent of a nonionic lipid selected from the group consisting of:
      i. glyceryl monoesters having a fatty acid chain containing from about 3 to about 50 carbon atoms;
      ii. glyceryl diesters having a fatty acid chain containing from about 5 carbon atoms to about 25 carbon atoms;
      iii. alkoxylated alcohols alkoxylated with ethylene oxide or propylene oxide;
      iv. alkoxylated alkyl phenols alkoxylated with ethylene oxide or propylene oxide;
      v. alkoxylated acids alkoxylated with ethylene oxide or propylene oxide;
      vi. alkoxylated amides alkoxylated with ethylene oxide or propylene oxide;
      vii. alkoxylated sugar derivatives alkoxylated with ethylene oxide or propylene oxide;
      viii. alkoxylated derivatives of natural oils or waxes alkoxylated with ethylene oxide or propylene oxide;
      ix. polyoxyethylene fatty ethers having a fatty acid chain containing from about 10 carbon atoms to about 18 carbon atoms;
      x. steroids;
      xi. fatty acid esters of alcohols where the fatty acid is straight or branched chain having from about 10 carbon atoms to about 20 carbon atoms and the alcohol is straight or branched chain having 1 to 10 carbon atoms; and
      xii. mixtures thereof;
   B. from about 74 percent to about 98 percent of a vehicle comprised of:
      1) a first vehicle component comprised of water; and
      2) a second vehicle component comprised of an alcohol, a polyol, or mixtures thereof; and
   C. an effective amount of the skin or hair benefit agent, wherein said micelle is comprised of said nonionic lipid and said second vehicle component and,
   wherein said benefit agent is selected from the group consisting of minoxidil, N"-cyano-N-(tert-pentyl)-N'-3-pyridinyl-guanidine, diazoxide, vitamin E, vitamin C, vitamin E acetate, vitamin C palmitate; erythropoietin; prostaglandin E1, prostaglandin F2-alpha, oleic acid, heat shock protein 27, heat shock protein 72, verapamil HCL, nifedipine, diltiazemamiloride, cyclosporin, Fk-506; finasteride, 17-beta estradiol, EGF, FGF, benoxaprofen, tretinoin, IL-6IL-1alpha, and IL-1beta ICAM, betametasone, aloe, clove, ginseng, rehmannia, swertia, sweet orange, zanthoxylum, elubiol, ketoconazole, zinc pyrithione, streptomycin, cycloheximide, and mixtures thereof.

3. A method for treating or minimizing the effects of aging comprising topically administering to a human or animal at a desired area a micellar composition comprising, based upon the total weight of the composition:
   A. from about 1 percent to about 10 percent of a nonionic lipid selected from the group consisting of:
      i. glyceryl monoesters having a fatty acid chain containing from about 3 to about 50 carbon atoms;
      ii. glyceryl diesters having a fatty acid chain containing from about 5 carbon atoms to about 25 carbon atoms;
      iii. alkoxylated alcohols alkoxylated with ethylene oxide or propylene oxide;
      iv. alkoxylated alkyl phenols alkoxylated with ethylene oxide or propylene oxide;
      v. alkoxylated acids alkoxylated with ethylene oxide or propylene oxide;
      vi. alkoxylated amides alkoxylated with ethylene oxide or propylene oxide;
      vii. alkoxylated sugar derivatives alkoxylated with ethylene oxide or propylene oxide;

viii. alkoxylated derivatives of natural oils or waxes alkoxylated with ethylene oxide or propylene oxide;
ix. polyoxyethylene fatty ethers having a fatty acid chain containing from about 10 carbon atoms to about 18 carbon atoms;
x. steroids;
xi. fatty acid esters of alcohols where the fatty acid is straight or branched chain having from about 10 carbon atoms to about 20 carbon atoms and the alcohol is straight or branched chain having 1 to 10 carbon atoms; and
xii. mixtures thereof;

B. from about 74 percent to about 98 percent of a vehicle comprised of:
1) a first vehicle component comprised of water; and
2) a second vehicle component comprised of an alcohol, a polyol, or mixtures thereof; and C. an effective amount of the skin or hair benefit agent, wherein said micelle is comprised of said nonionic lipid and said second vehicle component and,
wherein said benefit agent is selected from the group consisting of sunscreens, retinoids and derivatives thereof, vitamins and derivatives thereof, antioxidants, hydroxy acids, botanical extracts, and mixtures thereof.

4. A method for treating acne comprising topically administering to a human or animal at a desired area a micellar composition comprising, based upon the total weight of the composition:
A. from about 1 percent to about 10 percent of a nonionic lipid selected from the group consisting of:
i. glyceryl monoesters having a fatty acid chain containing from about 3 to about 50 carbon atoms;
ii. glyceryl diesters having a fatty acid chain containing from about 5 carbon atoms to about 25 carbon atoms;
iii. alkoxylated alcohols alkoxylated with ethylene oxide or propylene oxide;
iv. alkoxylated alkyl phenols alkoxylated with ethylene oxide or propylene oxide;
v. alkoxylated acids alkoxylated with ethylene oxide or propylene oxide;
vi. alkoxylated amides alkoxylated with ethylene oxide or propylene oxide;
vii. alkoxylated sugar derivatives alkoxylated with ethylene oxide or propylene oxide;
viii. alkoxylated derivatives of natural oils or waxes alkoxylated with ethylene oxide or propylene oxide;
ix. polyoxyethylene fatty ethers having a fatty acid chain containing from about 10 carbon atoms to about 18 carbon atoms;
x. steroids;
xi. fatty acid esters of alcohols where the fatty acid is straight or branched chain having from about 10 carbon atoms to about 20 carbon atoms and the alcohol is straight or branched chain having 1 to 10 carbon atoms; and
xii. mixtures thereof;

B. from about 74 percent to about 98 percent of a vehicle comprised of:
1) a first vehicle component comprised of water; and
2) a second vehicle component comprised of an alcohol, a polyol, or mixtures thereof; and C. an effective amount of the skin or hair benefit agent, wherein said micelle is comprised of said nonionic lipid and said second vehicle component and,
wherein said benefit agent is selected from the group consisting of imidazoles, retinoids, salicylic acid, benzoyl peroxide, antibiotics, antiandrogens, 5-alpha-reductase isotypes, anti-inflammatory agents, botanical extracts, and mixtures thereof.

5. A method for depigmenting skin comprising topically administering to a human or animal at a desired area a micellar composition comprising, based upon the total weight of the composition:
A. from about 1 percent to about 10 percent of a nonionic lipid selected from the group consisting of:
i. glyceryl monoesters having a fatty acid chain containing from about 3 to about 50 carbon atoms;
ii. glyceryl diesters having a fatty acid chain containing from about 5 carbon atoms to about 25 carbon atoms;
iii. alkoxylated alcohols alkoxylated with ethylene oxide or propylene oxide;
iv. alkoxylated alkyl phenols alkoxylated with ethylene oxide or propylene oxide;
v. alkoxylated acids alkoxylated with ethylene oxide or propylene oxide;
vi. alkoxylated amides alkoxylated with ethylene oxide or propylene oxide;
vii. alkoxylated sugar derivatives alkoxylated with ethylene oxide or propylene oxide;
viii. alkoxylated derivatives of natural oils or waxes alkoxylated with ethylene oxide or propylene oxide;
ix. polyoxyethylene fatty ethers having a fatty acid chain containing from about 10 carbon atoms to about 18 carbon atoms;
x. steroids;
xi. fatty acid esters of alcohols where the fatty acid is straight or branched chain having from about 10 carbon atoms to about 20 carbon atoms and the alcohol is straight or branched chain having 1 to 10 carbon atoms; and
xii. mixtures thereof;

B. from about 74 percent to about 98 percent of a vehicle comprised of:
1) a first vehicle component comprised of water; and
2) a second vehicle component comprised of an alcohol, a polyol, or mixtures thereof; and C. an effective amount of the skin or hair benefit agent, wherein said micelle is comprised of said nonionic lipid and said second vehicle component and,
wherein said benefit agent is selected from the group consisting of retinoids and derivatives thereof, kojic acid and its derivatives, hydroquinone and derivatives thereof, transexamic acid, vitamins, azelaic acid, botanical extracts, and mixtures thereof.

6. A method for treating the diseases of dandruff, seborrheic dermatitis, and psoriasis and/or the symptoms associated therewith comprising topically administering to a human or animal at a desired area a micellar composition comprising, based upon the total weight of the composition:
A. from about 1 percent to about 10 percent of a nonionic lipid selected from the group consisting of:
i. glyceryl monoesters having a fatty acid chain containing from about 3 to about 50 carbon atoms;
ii. glyceryl diesters having a fatty acid chain containing from about 5 carbon atoms to about 25 carbon atoms;
iii. alkoxylated alcohols alkoxylated with ethylene oxide or propylene oxide;
iv. alkoxylated alkyl phenols alkoxylated with ethylene oxide or propylene oxide;
v. alkoxylated acids alkoxylated with ethylene oxide or propylene oxide;
vi. alkoxylated amides alkoxylated with ethylene oxide or propylene oxide;

vii. alkoxylated sugar derivatives alkoxylated with ethylene oxide or propylene oxide;
viii. alkoxylated derivatives of natural oils or waxes alkoxylated with ethylene oxide or propylene oxide;
ix. polyoxyethylene fatty ethers having a fatty acid chain containing from about 10 carbon atoms to about 18 carbon atoms;
x. steroids;
xi. fatty acid esters of alcohols where the fatty acid is straight or branched chain having from about 10 carbon atoms to about 20 carbon atoms and the alcohol is straight or branched chain having 1 to 10 carbon atoms; and
xii. mixtures thereof;

B. from about 74 percent to about 98 percent of a vehicle comprised of:
   1) a first vehicle component comprised of water; and
   2) a second vehicle component comprised of an alcohol, a polyol, or mixtures thereof; and
C. an effective amount of the skin or hair benefit agent, wherein said micelle is comprised of said nonionic lipid and said second vehicle component and,
wherein said benefit agent is selected from the group consisting of zinc pyrithione, selenium sulfide, sulfur, sulfonated shale oil, salicylic acid, coal tar, povidone-iodine, imidazoles, piroctone olamine, selenium sulfide, ciclopirox olamine, anti-psoriasis agents, vitamin A deivatives, corticosteroids, and mixtures thereof.

7. A method of claim 1 wherein said nonionic lipid is selected from the group consisting of polyoxyethylene stearyl ether having from about 5 to about 10 oxyethylene units, a polyoxyethylene myristyl ether having from about 5 to about 10 oxyethylene units, a polyoxyethylene lauryl ether having from about 5 to about 10 oxyethylene units, a polyoxyethylene cetyl ether having from about 5 to about 10 oxyethylene units, isopropyl myristate, and mixtures thereof.

8. A method of claim 2 wherein said nonionic lipid is selected from the group consisting of polyoxyethylene stearyl ether having from about 5 to about 10 oxyethylene units, a polyoxyethylene myristyl ether having from about 5 to about 10 oxyethylene units, a polyoxyethylene lauryl ether having from about 5 to about 10 oxyethylene units, a polyoxyethylene cetyl ether having from about 5 to about 10 oxyethylene units, isopropyl myristate, and mixtures thereof.

9. A method of claim 3 wherein said nonionic lipid is selected from the group consisting of polyoxyethylene stearyl ether having from about 5 to about 10 oxyethylene units, a polyoxyethylene myristyl ether having from about 5 to about 10 oxyethylene units, a polyoxyethylene lauryl ether having from about 5 to about 10 oxyethylene units, a polyoxyethylene cetyl ether having from about 5 to about 10 oxyethylene units, isopropyl myristate, and mixtures thereof.

10. A method of claim 4 wherein said nonionic lipid is selected from the group consisting of polyoxyethylene stearyl ether having from about 5 to about 10 oxyethylene units, a polyoxyethylene myristyl ether having from about 5 to about 10 oxyethylene units, a polyoxyethylene lauryl ether having from about 5 to about 10 oxyethylene units, a polyoxyethylene cetyl ether having from about 5 to about 10 oxyethylene units, isopropyl myristate, and mixtures thereof.

11. A method of claim 5 wherein said nonionic lipid is selected from the group consisting of polyoxyethylene stearyl ether having from about 5 to about 10 oxyethylene units, a polyoxyethylene myristyl ether having from about 5 to about 10 oxyethylene units, a polyoxyethylene lauryl ether having from about 5 to about 10 oxyethylene units, a polyoxyethylene cetyl ether having from about 5 to about 10 oxyethylene units, isopropyl myristate, and mixtures thereof.

12. A method of claim 6 wherein said nonionic lipid is selected from the group consisting of polyoxyethylene stearyl ether having from about 5 to about 10 oxyethylene units, a polyoxyethylene myristyl ether having from about 5 to about 10 oxyethylene units, a polyoxyethylene lauryl ether having from about 5 to about 10 oxyethylene units, a polyoxyethylene cetyl ether having from about 5 to about 10 oxyethylene units, isopropyl myristate, and mixtures thereof.

13. A method of claim 7 wherein said nonionic lipid is polyoxyethylene-10-stearyl ether and said vehicle comprises a mixture of ethanol and propylene glycol.

14. A method of claim 8 wherein said nonionic lipid is polyoxyethylene-10-stearyl ether and said vehicle comprises a mixture of ethanol and propylene glycol.

15. A method of claim 9 wherein said nonionic lipid is polyoxyethylene-10-stearyl ether and said vehicle comprises a mixture of ethanol and propylene glycol.

16. A method of claim 10 wherein wherein said nonionic lipid is polyoxyethylene-10-stearyl ether and said vehicle comprises a mixture of ethanol and propylene glycol.

17. A method of claim 11 wherein said nonionic lipid is polyoxyethylene-10-stearyl ether and said vehicle comprises a mixture of ethanol and propylene glycol.

18. A method of claim 12 wherein said nonionic lipid is polyoxyethylene-10-stearyl ether and said vehicle comprises a mixture of ethanol and propylene glycol.

19. A method of claim 13 wherein said benefit agent is minoxidil.

20. A method of claim 13 wherein said benefit agent is minoxidil.

* * * * *

UNITED STATES PATENT AND TRADEMARK OFFICE
CERTIFICATE OF CORRECTION

PATENT NO. : 6,419,913 B1
DATED : July 16, 2002
INVENTOR(S) : Susan M. Niemiec et al.

It is certified that error appears in the above-identified patent and that said Letters Patent is hereby corrected as shown below:

Column 16,
Line 38, please delete the first occurrence of the word "wherein"

Column 36,
Line 41, please delete the first occurrence of the word "wherein"

Signed and Sealed this

Twenty-fourth Day of August, 2004

JON W. DUDAS
*Director of the United States Patent and Trademark Office*